US012146889B1

(12) United States Patent
Tabuteau (10) Patent No.: US 12,146,889 B1
(45) Date of Patent: *Nov. 19, 2024

(54) COMPOUNDS AND COMBINATIONS THEREOF FOR TREATING NEUROLOGICAL AND PSYCHIATRIC CONDITIONS

(71) Applicant: ANTECIP BIOVENTURES II LLC, New York, NY (US)

(72) Inventor: Herriot Tabuteau, New York, NY (US)

(73) Assignee: ANTECIP BIOVENTURES II LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/494,550

(22) Filed: Oct. 25, 2023

Related U.S. Application Data

(63) Continuation of application No. PCT/US2023/069655, filed on Jul. 5, 2023.

(60) Provisional application No. 63/359,143, filed on Jul. 7, 2022, provisional application No. 63/370,592, filed on Aug. 5, 2022, provisional application No. 63/396,182, filed on Aug. 8, 2022, provisional application No. 63/373,040, filed on Aug. 19, 2022, provisional application No. 63/401,541, filed on Aug. 26, 2022.

(51) Int. Cl.
| | | |
|---|---|---|
| *A61K 31/485* | (2006.01) | |
| *A61K 31/131* | (2006.01) | |
| *A61K 31/135* | (2006.01) | |
| *A61P 25/24* | (2006.01) | |
| *G01N 33/94* | (2006.01) | |
| *A61K 9/20* | (2006.01) | |

(52) U.S. Cl.
CPC ......... *G01N 33/942* (2013.01); *A61K 31/135* (2013.01); *A61K 31/485* (2013.01); *A61P 25/24* (2018.01); *A61K 9/20* (2013.01); *G01N 2800/52* (2013.01)

(58) Field of Classification Search
CPC .. A61K 31/485; A61K 31/131; A61K 31/138; A61P 25/24
USPC ...................... 546/74; 564/502; 514/289, 646
See application file for complete search history.

(56) References Cited

U.S. PATENT DOCUMENTS

| | | |
|---|---|---|
| 5,358,970 A | 10/1994 | Ruff et al. |
| 5,731,000 A | 3/1998 | Ruff et al. |
| 5,763,493 A | 6/1998 | Ruff et al. |
| 6,306,436 B1 | 10/2001 | Chungi et al. |
| 6,780,871 B2 | 8/2004 | Glick et al. |
| 8,088,786 B2 | 6/2012 | Mckinney et al. |
| 8,569,328 B1 | 10/2013 | Tabuteau |
| 9,168,234 B2 | 10/2015 | Tabuteau |
| 9,198,905 B2 | 12/2015 | Tabuteau |
| 9,205,083 B2 | 12/2015 | Tabuteau |
| 9,238,032 B2 | 1/2016 | Tabuteau |
| 9,278,095 B2 | 3/2016 | Tabuteau |
| 9,314,462 B2 | 4/2016 | Tabuteau |
| 9,370,513 B2 | 6/2016 | Tabuteau |
| 9,375,429 B2 | 6/2016 | Tabuteau |
| 9,402,843 B2 | 8/2016 | Tabuteau |
| 9,402,844 B2 | 8/2016 | Tabuteau |
| 9,408,815 B2 | 8/2016 | Tabuteau |
| 9,421,176 B1 | 8/2016 | Tabuteau |
| 9,457,023 B1 | 10/2016 | Tabuteau |
| 9,457,025 B2 | 10/2016 | Tabuteau |
| 9,474,731 B1 | 10/2016 | Tabuteau |
| 9,486,450 B2 | 11/2016 | Tabuteau |
| 9,700,528 B2 | 7/2017 | Tabuteau |
| 9,700,553 B2 | 7/2017 | Tabuteau |
| 9,707,191 B2 | 7/2017 | Tabuteau |
| 9,763,932 B2 | 9/2017 | Tabuteau |
| 9,861,595 B2 | 1/2018 | Tabuteau |
| 9,867,819 B2 | 1/2018 | Tabuteau |
| 9,968,568 B2 | 5/2018 | Tabuteau |
| 10,058,518 B2 | 8/2018 | Tabuteau |
| 10,064,857 B2 | 9/2018 | Tabuteau |

(Continued)

FOREIGN PATENT DOCUMENTS

| | | |
|---|---|---|
| BR | 102016010170 A2 | 11/2017 |
| EP | 4183391 A1 | 5/2023 |

(Continued)

OTHER PUBLICATIONS

Spravato (esketamine), Highlights of Prescribing Information, revised Jul. 2020.
Nuedexta (dextromethorphan hydrobromide and quinidine sulfate), Highlights of Prescribing Information, revised Dec. 2022.
Aplenzin (bupropion hydrobromide), Highlights of Prescribing Information, revised Mar. 2022.
Tod et al., Quantitative Prediction of Cytochrome P450 (CYP) 2D6-Mediated Drug Interactions, Clinical Pharmacokinetics, 50(8), 519-530, Aug. 2011.
Kotlyar et al., Inhibition of CYP2D6 Activity by Bupropion, Journal of Clinical Psychopharmacology, 25(2), 226-229, Jun. 2005.

(Continued)

*Primary Examiner* — Charanjit Aulakh
(74) *Attorney, Agent, or Firm* — PROCOPIO, CORY, HARGREAVES & SAVITCH LLP; Brent Johnson; Yuefen Zhou (57) ABSTRACT

This disclosure relates to administration of a combination of: 1) about 100-110 mg, about 104-106 mg, or about 105 mg or less of bupropion hydrochloride, or a molar equivalent amount of the free base form or another salt form of bupropion; and 2) about 40-50 mg, about 44-46 mg, or about 45 mg or less of dextromethorphan hydrobromide, or a molar equivalent amount of the free base form or another salt form of dextromethorphan in certain patient populations, such as patients having moderate renal impairment, patients receiving a concomitant strong CYP2D6 inhibitor, patients who are known CYP2D6 poor metabolizers, those in need of an NMDA antagonist that does not cause dissociation, and those at risk of QT prolongation.

16 Claims, 2 Drawing Sheets

(56) References Cited

U.S. PATENT DOCUMENTS

| | | |
|---|---|---|
| 10,080,727 B2 | 9/2018 | Tabuteau |
| 10,092,560 B2 | 10/2018 | Tabuteau |
| 10,092,561 B2 | 10/2018 | Tabuteau |
| 10,105,327 B2 | 10/2018 | Tabuteau |
| 10,105,361 B2 | 10/2018 | Tabuteau |
| 10,251,879 B2 | 4/2019 | Tabuteau |
| 10,463,634 B2 | 11/2019 | Tabuteau |
| 10,512,643 B2 | 12/2019 | Tabuteau |
| 10,548,857 B2 | 2/2020 | Tabuteau |
| 10,596,167 B2 | 3/2020 | Tabuteau |
| 10,688,066 B2 | 6/2020 | Tabuteau |
| 10,695,304 B2 | 6/2020 | Tabuteau |
| 10,772,850 B2 | 9/2020 | Tabuteau |
| 10,780,064 B2 | 9/2020 | Tabuteau |
| 10,780,066 B2 | 9/2020 | Tabuteau |
| 10,786,469 B2 | 9/2020 | Tabuteau |
| 10,786,496 B2 | 9/2020 | Tabuteau |
| 10,799,497 B2 | 10/2020 | Tabuteau |
| 10,806,710 B2 | 10/2020 | Tabuteau |
| 10,813,924 B2 | 10/2020 | Tabuteau |
| 10,864,209 B2 | 12/2020 | Tabuteau |
| 10,874,663 B2 | 12/2020 | Tabuteau |
| 10,874,664 B2 | 12/2020 | Tabuteau |
| 10,874,665 B2 | 12/2020 | Tabuteau |
| 10,881,624 B2 | 1/2021 | Tabuteau |
| 10,881,657 B2 | 1/2021 | Tabuteau |
| 10,894,046 B2 | 1/2021 | Tabuteau |
| 10,894,047 B2 | 1/2021 | Tabuteau |
| 10,898,453 B2 | 1/2021 | Tabuteau |
| 10,925,842 B2 | 2/2021 | Tabuteau |
| 10,933,034 B2 | 3/2021 | Tabuteau |
| 10,940,124 B2 | 3/2021 | Tabuteau |
| 10,945,973 B2 | 3/2021 | Tabuteau |
| 10,966,941 B2 | 4/2021 | Tabuteau |
| 10,966,942 B2 | 4/2021 | Tabuteau |
| 10,966,974 B2 | 4/2021 | Tabuteau |
| 10,980,800 B2 | 4/2021 | Tabuteau |
| 11,007,189 B2 | 5/2021 | Tabuteau |
| 11,020,389 B2 | 6/2021 | Tabuteau |
| 11,058,648 B2 | 7/2021 | Tabuteau |
| 11,065,248 B2 | 7/2021 | Tabuteau |
| 11,090,300 B2 | 8/2021 | Tabuteau |
| 11,096,937 B2 | 8/2021 | Tabuteau |
| 11,123,343 B2 | 9/2021 | Tabuteau |
| 11,123,344 B2 | 9/2021 | Tabuteau |
| 11,129,826 B2 | 9/2021 | Tabuteau |
| 11,141,388 B2 | 10/2021 | Tabuteau |
| 11,141,416 B2 | 10/2021 | Tabuteau |
| 11,147,808 B2 | 10/2021 | Tabuteau |
| 11,185,515 B2 | 11/2021 | Tabuteau |
| 11,191,739 B2 | 12/2021 | Tabuteau |
| 11,197,839 B2 | 12/2021 | Tabuteau |
| 11,207,281 B2 | 12/2021 | Tabuteau |
| 11,213,521 B2 | 1/2022 | Tabuteau |
| 11,229,640 B2 | 1/2022 | Tabuteau |
| 11,234,946 B2 | 2/2022 | Tabuteau |
| 11,253,491 B2 | 2/2022 | Tabuteau |
| 11,253,492 B2 | 2/2022 | Tabuteau |
| 11,273,133 B2 | 3/2022 | Tabuteau |
| 11,273,134 B2 | 3/2022 | Tabuteau |
| 11,285,118 B2 | 3/2022 | Tabuteau |
| 11,285,146 B2 | 3/2022 | Tabuteau |
| 11,291,638 B2 | 4/2022 | Tabuteau |
| 11,291,665 B2 | 4/2022 | Tabuteau |
| 11,298,351 B2 | 4/2022 | Tabuteau |
| 11,298,352 B2 | 4/2022 | Tabuteau |
| 11,311,534 B2 | 4/2022 | Tabuteau |
| 11,344,544 B2 | 5/2022 | Tabuteau |
| 11,357,744 B2 | 6/2022 | Tabuteau |
| 11,364,233 B2 | 6/2022 | Tabuteau |
| 11,382,874 B2 | 7/2022 | Tabuteau |
| 11,419,867 B2 | 8/2022 | Tabuteau |
| 11,426,370 B2 | 8/2022 | Tabuteau |
| 11,426,401 B2 | 8/2022 | Tabuteau |
| 11,433,067 B2 | 9/2022 | Tabuteau |
| 11,439,636 B1 | 9/2022 | Tabuteau |
| 11,478,468 B2 | 10/2022 | Tabuteau |
| 11,497,721 B2 | 11/2022 | Tabuteau |
| 11,510,918 B2 | 11/2022 | Tabuteau |
| 11,517,542 B2 | 12/2022 | Tabuteau |
| 11,517,543 B2 | 12/2022 | Tabuteau |
| 11,517,544 B2 | 12/2022 | Tabuteau |
| 11,524,007 B2 | 12/2022 | Tabuteau |
| 11,524,008 B2 | 12/2022 | Tabuteau |
| 11,534,414 B2 | 12/2022 | Tabuteau |
| 11,541,021 B2 | 1/2023 | Tabuteau |
| 11,541,048 B2 | 1/2023 | Tabuteau |
| 11,571,399 B2 | 2/2023 | Tabuteau |
| 11,571,417 B2 | 2/2023 | Tabuteau |
| 11,576,877 B2 | 2/2023 | Tabuteau |
| 11,576,909 B2 | 2/2023 | Tabuteau |
| 11,590,124 B2 | 2/2023 | Tabuteau |
| 11,596,627 B2 | 3/2023 | Tabuteau |
| 11,617,728 B2 | 4/2023 | Tabuteau |
| 11,617,747 B2 | 4/2023 | Tabuteau |
| 11,628,149 B2 | 4/2023 | Tabuteau |
| 11,660,273 B2 | 5/2023 | Tabuteau |
| 11,660,274 B2 | 5/2023 | Tabuteau |
| 11,717,518 B1 | 8/2023 | Tabuteau |
| 11,730,706 B1 | 8/2023 | Tabuteau |
| 11,752,144 B1 | 9/2023 | Tabuteau |
| 11,779,579 B2 | 10/2023 | Tabuteau |
| 11,839,612 B1 * | 12/2023 | Tabuteau ............ A61K 9/2013 |
| 11,844,797 B1 | 12/2023 | Tabuteau |
| 11,883,373 B1 | 1/2024 | Tabuteau |
| 11,896,563 B2 | 2/2024 | Tabuteau |
| 11,925,636 B2 | 3/2024 | Tabuteau |
| 2002/0035105 A1 | 3/2002 | Caruso |
| 2003/0044462 A1 | 3/2003 | Subramanian et al. |
| 2008/0044462 A1 | 2/2008 | Trumbore et al. |
| 2010/0040679 A1 | 2/2010 | Chang |
| 2010/0291225 A1 | 11/2010 | Fanda et al. |
| 2015/0126541 A1 | 5/2015 | Tabuteau |
| 2015/0126542 A1 | 5/2015 | Tabuteau |
| 2015/0126543 A1 | 5/2015 | Tabuteau |
| 2015/0126544 A1 | 5/2015 | Tabuteau |
| 2015/0133485 A1 | 5/2015 | Tabuteau |
| 2015/0133486 A1 | 5/2015 | Tabuteau |
| 2015/0150830 A1 | 6/2015 | Tabuteau |
| 2015/0157582 A1 | 6/2015 | Tabuteau |
| 2015/0342947 A1 | 12/2015 | Pollard et al. |
| 2016/0008352 A1 | 1/2016 | Tabuteau |
| 2016/0030420 A1 | 2/2016 | Tabuteau |
| 2016/0030421 A1 | 2/2016 | Tabuteau |
| 2016/0128944 A1 | 5/2016 | Chawrai et al. |
| 2016/0128998 A1 | 5/2016 | Tabuteau |
| 2016/0136155 A1 | 5/2016 | Tabuteau |
| 2016/0199321 A1 | 7/2016 | Tabuteau |
| 2016/0228390 A1 | 8/2016 | Tabuteau |
| 2016/0263099 A1 | 9/2016 | Tabuteau |
| 2016/0263100 A1 | 9/2016 | Tabuteau |
| 2016/0317475 A1 | 11/2016 | Tabuteau |
| 2016/0317476 A1 | 11/2016 | Tabuteau |
| 2016/0324807 A1 | 11/2016 | Tabuteau |
| 2016/0339017 A1 | 11/2016 | Tabuteau |
| 2016/0346276 A1 | 12/2016 | Tabuteau |
| 2016/0361305 A1 | 12/2016 | Tabuteau |
| 2016/0375008 A1 | 12/2016 | Tabuteau |
| 2016/0375012 A1 | 12/2016 | Tabuteau |
| 2017/0007558 A1 | 1/2017 | Tabuteau |
| 2017/0014357 A1 | 1/2017 | Tabuteau |
| 2017/0252309 A1 | 9/2017 | Tabuteau |
| 2017/0281617 A1 | 10/2017 | Tabuteau |
| 2017/0304229 A1 | 10/2017 | Tabuteau |
| 2017/0304230 A1 | 10/2017 | Tabuteau |
| 2017/0304298 A1 | 10/2017 | Tabuteau |
| 2017/0354619 A1 | 12/2017 | Tabuteau |
| 2017/0360773 A1 | 12/2017 | Tabuteau |
| 2017/0360774 A1 | 12/2017 | Tabuteau |
| 2017/0360776 A1 | 12/2017 | Tabuteau |
| 2018/0092906 A1 | 4/2018 | Tabuteau |
| 2018/0116980 A1 | 5/2018 | Tabuteau |
| 2018/0133195 A1 | 5/2018 | Tabuteau |
| 2018/0207151 A1 | 7/2018 | Tabuteau |

(56) References Cited

U.S. PATENT DOCUMENTS

| | | |
|---|---|---|
| 2018/0256518 A1 | 9/2018 | Tabuteau |
| 2018/0360823 A1 | 12/2018 | Tabuteau |
| 2019/0000835 A1 | 1/2019 | Tabuteau |
| 2019/0008800 A1 | 1/2019 | Tabuteau |
| 2019/0008801 A1 | 1/2019 | Tabuteau |
| 2019/0008805 A1 | 1/2019 | Tabuteau |
| 2019/0015407 A1 | 1/2019 | Tabuteau |
| 2019/0083426 A1 | 3/2019 | Tabuteau |
| 2019/0142768 A1 | 5/2019 | Tabuteau |
| 2019/0192450 A1 | 6/2019 | Tabuteau |
| 2019/0192507 A1 | 6/2019 | Tabuteau |
| 2019/0216798 A1 | 7/2019 | Tabuteau |
| 2019/0216800 A1 | 7/2019 | Tabuteau |
| 2019/0216801 A1 | 7/2019 | Tabuteau |
| 2019/0290601 A1 | 9/2019 | Tabuteau |
| 2020/0022929 A1 | 1/2020 | Tabuteau |
| 2020/0093762 A1 | 3/2020 | Tabuteau |
| 2020/0147008 A1 | 5/2020 | Tabuteau |
| 2020/0147075 A1 | 5/2020 | Tabuteau |
| 2020/0206217 A1 | 7/2020 | Tabuteau |
| 2020/0215055 A1 | 7/2020 | Tabuteau |
| 2020/0215056 A1 | 7/2020 | Tabuteau |
| 2020/0215057 A1 | 7/2020 | Tabuteau |
| 2020/0215058 A1 | 7/2020 | Tabuteau |
| 2020/0215059 A1 | 7/2020 | Tabuteau |
| 2020/0222389 A1 | 7/2020 | Tabuteau |
| 2020/0230078 A1 | 7/2020 | Tabuteau |
| 2020/0230129 A1 | 7/2020 | Tabuteau |
| 2020/0230130 A1 | 7/2020 | Tabuteau |
| 2020/0230131 A1 | 7/2020 | Tabuteau |
| 2020/0237751 A1 | 7/2020 | Tabuteau |
| 2020/0237752 A1 | 7/2020 | Tabuteau |
| 2020/0246280 A1 | 8/2020 | Tabuteau |
| 2020/0261431 A1 | 8/2020 | Tabuteau |
| 2020/0297666 A1 | 9/2020 | Tabuteau |
| 2020/0338022 A1 | 10/2020 | Tabuteau |
| 2020/0360310 A1 | 11/2020 | Tabuteau |
| 2020/0397723 A1 | 12/2020 | Tabuteau |
| 2020/0397724 A1 | 12/2020 | Tabuteau |
| 2020/0405664 A1 | 12/2020 | Tabuteau |
| 2021/0000763 A1 | 1/2021 | Tabuteau |
| 2021/0000764 A1 | 1/2021 | Tabuteau |
| 2021/0000765 A1 | 1/2021 | Tabuteau |
| 2021/0000768 A1 | 1/2021 | Tabuteau |
| 2021/0000820 A1 | 1/2021 | Tabuteau |
| 2021/0015768 A1 | 1/2021 | Tabuteau |
| 2021/0015814 A1 | 1/2021 | Tabuteau |
| 2021/0015815 A1 | 1/2021 | Tabuteau |
| 2021/0023075 A1 | 1/2021 | Tabuteau |
| 2021/0023076 A1 | 1/2021 | Tabuteau |
| 2021/0030747 A1 | 2/2021 | Tabuteau |
| 2021/0030749 A1 | 2/2021 | Tabuteau |
| 2021/0030750 A1 | 2/2021 | Tabuteau |
| 2021/0030751 A1 | 2/2021 | Tabuteau |
| 2021/0046067 A1 | 2/2021 | Tabuteau |
| 2021/0052521 A1 | 2/2021 | Tabuteau |
| 2021/0060004 A1 | 3/2021 | Tabuteau |
| 2021/0060005 A1 | 3/2021 | Tabuteau |
| 2021/0069125 A1 | 3/2021 | Tabuteau |
| 2021/0069128 A1 | 3/2021 | Tabuteau |
| 2021/0077428 A1 | 3/2021 | Tabuteau |
| 2021/0077429 A1 | 3/2021 | Tabuteau |
| 2021/0077483 A1 | 3/2021 | Tabuteau |
| 2021/0106546 A1 | 4/2021 | Tabuteau |
| 2021/0177834 A1 | 6/2021 | Tabuteau |
| 2021/0186899 A1 | 6/2021 | Tabuteau |
| 2021/0186900 A1 | 6/2021 | Tabuteau |
| 2021/0186901 A1 | 6/2021 | Tabuteau |
| 2021/0186955 A1 | 6/2021 | Tabuteau |
| 2021/0186956 A1 | 6/2021 | Tabuteau |
| 2021/0196704 A1 | 7/2021 | Tabuteau |
| 2021/0196705 A1 | 7/2021 | Tabuteau |
| 2021/0205239 A1 | 7/2021 | Tabuteau |
| 2021/0205240 A1 | 7/2021 | Tabuteau |
| 2021/0205297 A1 | 7/2021 | Tabuteau |
| 2021/0220293 A1 | 7/2021 | Tabuteau |
| 2021/0220294 A1 | 7/2021 | Tabuteau |
| 2021/0220348 A1 | 7/2021 | Tabuteau |
| 2021/0260054 A1 | 8/2021 | Tabuteau |
| 2021/0267967 A1 | 9/2021 | Tabuteau |
| 2021/0338605 A1 | 11/2021 | Tabuteau |
| 2021/0346370 A1 | 11/2021 | Tabuteau |
| 2021/0361645 A1 | 11/2021 | Tabuteau |
| 2021/0401828 A1 | 12/2021 | Tabuteau |
| 2021/0401829 A1 | 12/2021 | Tabuteau |
| 2021/0401830 A1 | 12/2021 | Tabuteau |
| 2021/0401831 A1 | 12/2021 | Tabuteau |
| 2022/0008363 A1 | 1/2022 | Tabuteau |
| 2022/0071930 A1 | 3/2022 | Tabuteau |
| 2022/0071931 A1 | 3/2022 | Tabuteau |
| 2022/0079892 A1 | 3/2022 | Tabuteau |
| 2022/0096462 A1 | 3/2022 | Tabuteau |
| 2022/0105086 A1 | 4/2022 | Tabuteau |
| 2022/0133655 A1 | 5/2022 | Tabuteau |
| 2022/0142950 A1 | 5/2022 | Tabuteau |
| 2022/0193012 A1 | 6/2022 | Tabuteau |
| 2022/0218631 A1 | 7/2022 | Tabuteau |
| 2022/0218698 A1 | 7/2022 | Tabuteau |
| 2022/0233470 A1 | 7/2022 | Tabuteau |
| 2022/0233474 A1 | 7/2022 | Tabuteau |
| 2022/0233518 A1 | 7/2022 | Tabuteau |
| 2022/0233519 A1 | 7/2022 | Tabuteau |
| 2022/0241220 A1 | 8/2022 | Tabuteau |
| 2022/0241221 A1 | 8/2022 | Tabuteau |
| 2022/0241269 A1 | 8/2022 | Tabuteau |
| 2022/0241270 A1 | 8/2022 | Tabuteau |
| 2022/0265639 A1 | 8/2022 | Tabuteau |
| 2022/0280504 A1 | 9/2022 | Tabuteau |
| 2022/0313689 A1 | 10/2022 | Tabuteau |
| 2022/0323381 A1 | 10/2022 | Tabuteau |
| 2022/0378779 A1 | 12/2022 | Tabuteau |
| 2023/0045675 A1 | 2/2023 | Tabuteau |
| 2023/0096437 A1 | 3/2023 | Tabuteau |
| 2023/0099206 A1 | 3/2023 | Tabuteau |
| 2023/0100008 A1 | 3/2023 | Tabuteau |
| 2023/0100913 A1 | 3/2023 | Tabuteau |
| 2023/0114111 A1 | 4/2023 | Tabuteau |
| 2023/0131854 A1 | 4/2023 | Tabuteau |
| 2023/0142244 A1 | 5/2023 | Tabuteau |
| 2023/0210843 A1 | 7/2023 | Tabuteau |
| 2023/0218550 A1 | 7/2023 | Tabuteau |
| 2023/0225995 A1 | 7/2023 | Tabuteau |
| 2023/0233491 A1 | 7/2023 | Tabuteau |
| 2023/0241010 A1 | 8/2023 | Tabuteau |
| 2023/0248668 A1 | 8/2023 | Tabuteau |
| 2023/0248669 A1 | 8/2023 | Tabuteau |
| 2023/0255905 A1 | 8/2023 | Tabuteau |
| 2023/0263750 A1 | 8/2023 | Tabuteau |
| 2023/0270740 A1 | 8/2023 | Tabuteau |
| 2023/0277478 A1 | 9/2023 | Tabuteau |
| 2023/0277479 A1 | 9/2023 | Tabuteau |
| 2023/0277480 A1 | 9/2023 | Tabuteau |
| 2023/0277481 A1 | 9/2023 | Tabuteau |
| 2023/0293456 A1 | 9/2023 | Tabuteau |
| 2024/0000770 A1 | 1/2024 | Tabuteau |
| 2024/0016797 A1 | 1/2024 | Tabuteau |
| 2024/0024309 A1 | 1/2024 | Tabuteau |
| 2024/0041862 A1 | 2/2024 | Tabuteau |
| 2024/0041863 A1 | 2/2024 | Tabuteau |
| 2024/0050383 A1 | 2/2024 | Tabuteau |
| 2024/0189302 A1 | 6/2024 | Tabuteau |
| 2024/0197656 A1 | 6/2024 | Tabuteau |
| 2024/0197720 A1 | 6/2024 | Tabuteau |

FOREIGN PATENT DOCUMENTS

| | | |
|---|---|---|
| KR | 101612197 B1 | 4/2016 |
| WO | 1998050044 | 11/1998 |
| WO | 2003086362 A2 | 10/2003 |
| WO | 2004089873 A1 | 10/2004 |
| WO | 2009006194 | 1/2009 |
| WO | 2009050726 A2 | 4/2009 |
| WO | 2015069809 A1 | 5/2015 |
| WO | 2016125108 A1 | 8/2016 |

(56) References Cited

FOREIGN PATENT DOCUMENTS

| WO | 2020146412 A1 | 7/2020 |
| WO | 2021202329 A1 | 10/2021 |
| WO | 2021202419 A1 | 10/2021 |
| WO | 2022119981 A1 | 6/2022 |
| WO | 2023004064 A1 | 1/2023 |

OTHER PUBLICATIONS

Pope et al., Pharmacokinetics of Dextromethorphan after Single or Multiple Dosing in Combination with Quinidine in Extensive and Poor Metabolizers, The Journal of Clinical Pharmacology, 44(10), 1132-1142, Oct. 2004.
Auvelity (dextromethorphan hydrobromide and bupropion hydrochloride), Highlights of Prescribing Information and Medication Guide, issued Dec. 2022.
International Preliminary Report on Patentability, PCT/US2021/061492, mailed on Jun. 15, 2023.
International Search Report and Written Opinion, PCT/US2021/061492.
International Search Report and Written Opinion, PCT/US2022/012768.
International Search Report and Written Opinion, PCT/US2023/067062 mailed on Jul. 12, 2023.
Axsome Therapeutics Announces Topline Results of the Stride-1 Phase 3 Trial in Treatment Resistant Depression and Expert Call to Discuss Clinical Implications, Mar. 2020 (retrieved from internet on Jul. 19, 2023). <axsometherapeuticsinc.gcs-web.com/node/9176/pdf>.
Anderson, A.; et al. "Efficacy and Safety of AXS-05, an Oral NMDA Receptor Antagonist with Multimodal Activity, in Major Depressive Disorder: Results of a Phase 2, Double-Blind, Active-Controlled Trial" ASCP Annual Meeting 2019 (retrieved from internet on Jul. 19, 2023). <d3dyybxyjb4kyh.cloudfront.net/pdfs/SOBP+2021+AXS-05+MDD+Poster+FINAL.pdf> (May 2019).
O'Gorman, C; et al. "Rapid Effects of AXS 05, an Oral NMDA Receptor Antagonist, in Major Depressive Disorder: Results from Two Randomized, Double Blind, Controlled Trials" ASCP Annual Meeting 2021 (retrieved from internet on Jul. 19, 2023). <d3dyybxyjb4kyh.cloudfront.net/pdfs/SOBP+2021+AXS-05+MDD+Poster+FINAL.pdf> (Jun. 2021).
O'Gorman, C.; et al. "PMH40 Effects of AXS-05 on Patient Reported Depressive Symptoms in Major Depressive Disorder: Results from the Gemini Trial" <doi.org/10.1016/j.jval.2021.04.662> (retrieved from internet on Jul. 19, 2023). Value in Health, Jun. 2021, vol. 24, Supplement 1, pp. S135.
O'Gorman, C.; et al. "P246. Rapid Antidepressant Effects and MADRS Core Symptom Improvements With AXS-05, an Oral NMDA Receptor Antagonist, in Major Depressive Disorder: Results From Two Randomized, Double-Blind, Controlled Trials" ACNP 60th Annual Meeting: Poster Abstracts P246 <nature.com/articles/s41386-021-01236-7> (retrieved from internet on Jul. 19, 2023). Neuropsychopharmacol. 46 (Suppl 1), 72-217, Dec. 2021.
International Preliminary Report on Patentability, PCT/US2022/012768, mailed on Jul. 27, 2023.
Nofziger et al., Evaluation of dextromethorphan with select antidepressant therapy for the treatment of depression in the acute care psychiatric setting, Mental Health Clinician, 9(2), 76-81, Mar. 2019.
Update: Bupropion Hydrochloride Extended-Release 300 mg Bioequivalence Studies, FDA, retrieved Mar. 2021.
FDA Draft Guidance on Bupropion Hydrochloride, revised Mar. 2013.
Forfivo XL (bupropion hydrochloride) extended-release tablets, for oral use, Highlights of Prescribing Information, revised Dec. 2019.
Forfivo XL (Bupropion HCl) extended-release tablet, NDA 22497, Jan. 25, 2010.
Wellbutrin XL (bupropion hydrochloride extended-release), Highlights of Prescribing Information, revised Mar. 2022.
Baker T. E. et al., Human Milk and Plasma Pharmacokinetics of Single-Dose Rimegepant 75mg in Healthy Lactating Women, Breastfeeding Medicine, 17(3), 277-282, 2022.
Berle J. O. et al., Antidepressant Use During Breastfeeding, Current Women's Health Reviews, 7(1), 28-34, Feb. 2011.
Briggs G. G. et al., Excretion of bupropion in breast milk, Annals of Pharmacotherapy, 27(4):431-433, Apr. 1993.
Chad L. et al., Update on antidepressant use during breastfeeding, Canadian Family Physician, 59(6), 633-634, Jun. 2013.
Chaudron L. H. et al., Bupropion and Breastfeeding: A case of a possible Infant Seizure, The Journal of clinical psychiatry, 65(6), 881-882, Jun. 2004.
Davis M. F. et al., Bupropion Levels in Breast Milk for 4 Mother-Infant Pairs: More Answers to Lingering Questions, J. Clin. Psychiatry, 70(2), 297-298, Feb. 2009.
Di Scalea T. L. et al., Antidepressant Medication Use during Breastfeeding, Clinical obstetrics and gynecology, 52(3): 483-497, Sep. 2009.
Dwoskin L. P. et al., Review of the Pharmacology and Clinical Profile of Bupropion, and Antidepressant and Tobacco Use Cessation Agent, CNS Drug Reviews, 12(3-4), 178-207, Sep. 2006.
Gentile S, The safety of newer antidepressants in pregnancy and breastfeeding, Drug Safety, 28(2),137-152, Feb. 2005. [doi: 10.2165/00002018-200528020-00005. PMID: 15691224.].
Haas J. S. et al., Bupropion in breast milk: an exposure assessment for potential treatment to prevent post-partum tobacco use, Tobacco Control, 13(1), 52-56, Mar. 2004.
Ram D. et al., Antidepressants, anxiolytics, and hypnotics in pregnancy and lactation, Indian J Psychiatry, 57(Suppl 2): S354-S371, Jul. 2015. [doi: 10.4103/0019-5545.161504].
Weissman A. M. et al., Pooled Analysis of Antidepressant Levels in Lactating Mothers, Breast Milk, and Nursing Infants, Am J Psychiatry, 161(6), 1066-1078, Jun. 2004.
Horn J. R. et al., Get to Know an Enzyme: CYP2D6, Pharmacy Times, Jul. 2008, retrieved on Aug. 28, 2023.
International Search Report and Written Opinion, PCT/US2023/069286 mailed on Aug. 22, 2023.
International Search Report and Written Opinion, PCT/US2023/069239 mailed on Aug. 28, 2023.
International Search Report and Written Opinion, PCT/US2023/069367 mailed on Aug. 28, 2023.
International Search Report and Written Opinion, PCT/US2023/069655 mailed on Sep. 15, 2023.
International Search Report and Written Opinion, PCT/US2023/069371 mailed on Sep. 26, 2023.
International Search Report and Written Opinion, PCT/US2022/037913 mailed on Sep. 21, 2022.
Jones A et al., "Early Improvements in Functioning and Quality of Life With AXS-05 in Major Depressive Disorder: Results From the Gemini Trial ," Value in Health, Jun. 2021, vol. 24, abstract No. PHM42, p. S135. DOI: 10.1016/j.jval.2021.04.662.
International Search Report and Written Opinion, PCT/US2022/074713 mailed on Sep. 21, 2022.
Axsome Therapeutics, Inc.: "Merit: A Randomized, Double-blind, Placebo-controlled Study of AXS-05 for Relapse Prevention in Treatment Resistant Depression," ClinicalTrials.gov, NCT04608396 version 2, Mar. 24, 2021.
International Preliminary Report on Patentability, PCT/US2022/037913, issued on Jan. 18, 2024.
International Preliminary Report on Patentability, PCT/US2022/074713, issued on Feb. 22, 2024.
Chinese Pat. No. 202080004041.1 Invalidation Notice and Request issued on Jan. 15, 2024. (English translation included).

* cited by examiner

COMPOUNDS AND COMBINATIONS THEREOF FOR TREATING NEUROLOGICAL AND PSYCHIATRIC CONDITIONS

CROSS-REFERENCE TO RELATED APPLICATIONS

This application is a continuation of International Pat. App. No. PCT/US2023/069655, filed Jul. 5, 2023; which claims benefit of U.S. Provisional App. Nos. 63/359,143, filed Jul. 7, 2022; 63/370,592, filed Aug. 5, 2022; 63/396,182, filed Aug. 8, 2022; 63/373,040, filed Aug. 19, 2022; and 63/401,541, filed Aug. 26, 2022.

SUMMARY

This disclosure relates to administration of a combination of: 1) about 100-110 mg, about 104-106 mg, or about 105 mg of bupropion hydrochloride, or a molar equivalent amount of a free base form or another salt form of dextromethorphan; and 2) about 40-50 mg, about 44-46 mg, or about 45 mg of dextromethorphan hydrobromide, or a molar equivalent amount of a free base form or another salt form of dextromethorphan in certain patient populations.

Some embodiments include a method of reducing the risk of neurotoxicity to a human child, comprising: i) administering a combination of about 45 mg of dextromethorphan hydrobromide and about 105 mg of bupropion hydrochloride to a human patient once daily or twice daily, wherein the human patient is a lactating mother of the human child and is experiencing major depressive disorder; and ii) advising the human patient not to breastfeed the human child while the combination is being administered to the human patient and for 5 days following the final dose of the combination.

Some embodiments include a method of treating major depressive disorder in a patient having moderate renal impairment, comprising administering a daily dose of: (i) about 105 mg of bupropion hydrochloride and (ii) about 45 mg of dextromethorphan hydrobromide to a human patient who has moderate renal impairment and is experiencing major depressive disorder.

Some embodiments include a method of treating a patient having a nervous system condition by administering a combination of dextromethorphan and bupropion, the method comprising:
orally administering to the patient, once a day, a dosage form comprising: 105 mg or less of bupropion hydrochloride, or a molar equivalent amount of the free base or another salt form of bupropion, and 45 mg or less of dextromethorphan hydrobromide, or a molar equivalent amount of the free base or another salt form of dextromethorphan, wherein the molar ratio of the bupropion to the dextromethorphan in the dosage form is about the ratio of the molar amount bupropion in 105 mg of bupropion hydrochloride to the molar amount of dextromethorphan in 45 mg of dextromethorphan hydrobromide;
wherein the patient is selected for: 1) having the nervous system condition and 2) having moderate renal impairment, wherein the patient is determined to have moderate renal impairment by an assay on a biological sample from the patient; and
wherein a risk of somnolence or dizziness for the patient who has moderate renal impairment is lower following orally administering the dosage form containing the combination once a day to the patient than it would be if a combination of 105 mg of bupropion hydrochloride and 45 mg of dextromethorphan hydrobromide were administered twice a day to the patient for the same number of days.

Some embodiments include a method of treating a patient with a combination of dextromethorphan and bupropion, wherein the patient is experiencing a nervous system condition, the method comprising the steps of:
determining whether the patient has moderate renal impairment by:
obtaining or having obtained a biological sample from the patient; and
performing or having performed an assay on the biological sample to determine if the patient has moderate renal impairment; and
if the patient has moderate renal impairment, then orally administering once a day to the patient, a dosage form containing a combination of 105 mg or less of bupropion hydrochloride, or a molar equivalent amount of the free base or another salt form of bupropion, and 45 mg or less of dextromethorphan hydrobromide, or a molar equivalent amount of the free base or another salt form of dextromethorphan, wherein the molar ratio of the bupropion to the dextromethorphan is about the ratio of the molar amount of bupropion in 105 mg of bupropion hydrochloride to the molar amount of dextromethorphan in 45 mg of dextromethorphan hydrobromide;
if the patient does not have renal impairment, then orally administering twice a day to the patient, a dosage form containing a combination of 105 mg of bupropion hydrochloride, or a molar equivalent amount of the free base or another salt form of bupropion, and 45 mg of dextromethorphan hydrobromide, or a molar equivalent amount of the free base or another salt form of dextromethorphan;
wherein a risk of somnolence or dizziness for a patient who has moderate renal impairment is lower following orally administering the dosage form containing the combination once a day to the patient than it would be if a combination of 105 mg of bupropion hydrochloride and 45 mg of dextromethorphan hydrobromide were administered twice a day to the patient for the same number of days.

Some embodiments include a method of treating a patient who is experiencing a nervous system condition, the method comprising the steps of:
a) determining whether the patient is at risk of an adverse event associated with overexposure to dextromethorphan by:
obtaining or having obtained a biological sample from the patient; and performing or having performed an assay on the biological sample to determine if the patient has moderate renal impairment, wherein a result that the patient has moderate renal impairment indicates that the patient is at risk of an adverse event associated with overexposure to dextromethorphan; and
b) if the patient is at risk of an adverse event associated with overexposure to dextromethorphan, then orally administering once a day to the patient, a dosage form containing a combination of 105 mg or less of bupropion hydrochloride, or a molar equivalent amount of the free base or another salt form of bupropion, and 45 mg or less of dextromethorphan hydrobromide, or a molar equivalent amount of the free base or another salt form of dextromethorphan, wherein the molar ratio of the bupropion to the dextromethorphan is about the ratio the molar amount of bupropion in 105 mg of bupropion hydrochloride to the molar amount of dextromethorphan in 45 mg of dextromethorphan hydrobromide; and c) if the patient is not at risk of an adverse event associated with overexposure to dextromethorphan, then orally administering twice a day to the patient, a dosage form containing a combination of 105 mg of bupropion hydrochloride, or a molar equivalent amount of the free base or another salt form of bupropion, and 45 mg of dextromethorphan hydrobromide, or a molar equivalent amount of the free base or another salt form of dextromethorphan.

Some embodiments include a method of treating a nervous system condition with a combination of dextromethorphan and bupropion, comprising:

orally administering to a patient, once a day, a dosage form containing a combination of 105 mg or less of bupropion hydrochloride, or a molar equivalent amount of the free base or another salt form of bupropion, and 45 mg or less of dextromethorphan hydrobromide, or a molar equivalent amount of the free base or another salt form of dextromethorphan, wherein the molar ratio of bupropion to dextromethorphan in the dosage form is about the ratio of the molar amount of bupropion in 105 mg of bupropion hydrochloride to the molar amount of dextromethorphan in 45 mg of dextromethorphan hydrobromide; and wherein the patient is selected for: 1) having the nervous system condition and 2) having moderate renal impairment, wherein the patient is determined to have moderate renal impairment by an assay on a biological sample from the patient; and wherein the patient has a reduced risk of an adverse event as compared with the risk of the adverse event that the patient would have if the dosage form were administered twice daily to the patient.

Some embodiments include a method of treating a patient with a combination of dextromethorphan and bupropion, wherein the patient is experiencing a nervous system condition, the method comprising the steps of:

determining whether the patient has moderate renal impairment by:

obtaining or having obtained a biological sample from the patient; and performing or having performed an assay on the biological sample to determine if the patient has moderate renal impairment; and if the patient has moderate renal impairment, then orally administering once a day to the patient, a dosage form containing a combination of 105 mg or less of bupropion hydrochloride, or a molar equivalent amount of the free base or another salt form of bupropion, and 45 mg or less of dextromethorphan hydrobromide, or a molar equivalent amount of the free base or another salt form of dextromethorphan, wherein the molar ratio of bupropion to dextromethorphan in the dosage form is about the ratio of the molar amount of bupropion in 105 mg of bupropion hydrochloride to the molar amount of dextromethorphan in 45 mg of dextromethorphan hydrobromide; and if the patient does not have renal impairment, then orally administering twice a day to the patient, a dosage form containing a combination of 105 mg of bupropion hydrochloride, or a molar equivalent amount of the free base or another salt form of bupropion, and 45 mg of dextromethorphan hydrobromide, or a molar equivalent amount of the free base or another salt form of dextromethorphan.

Some embodiments include a method of treating a patient having a nervous system condition by administering a combination of dextromethorphan and bupropion, the method comprising:

orally administering to the patient, once a day, a dosage form comprising: 105 mg or less of bupropion hydrochloride, or a molar equivalent amount of the free base or another salt form of bupropion, and 45 mg or less of dextromethorphan hydrobromide, or a molar equivalent amount of the free base or another salt form of dextromethorphan, wherein the molar ratio of the bupropion to the dextromethorphan in the dosage form is about the ratio of the molar amount bupropion in 105 mg of bupropion hydrochloride to the molar amount of dextromethorphan in 45 mg of dextromethorphan hydrobromide;

wherein the patient is selected for: 1) having the nervous system condition and 2) having moderate renal impairment, wherein the patient is determined to have moderate renal impairment by an assay on a biological sample from the patient; and wherein a risk of somnolence and dizziness for the patient who has moderate renal impairment is lower following orally administering the dosage form containing the combination once a day to the patient than it would be if a combination of 105 mg of bupropion hydrochloride and 45 mg of dextromethorphan hydrobromide were administered twice a day to the patient for the same number of days.

Some embodiments include a method of treating a patient with a combination of dextromethorphan and bupropion, wherein the patient is experiencing a nervous system condition, the method comprising the steps of:

determining whether the patient has moderate renal impairment by:

obtaining or having obtained a biological sample from the patient; and performing or having performed an assay on the biological sample to determine if the patient has moderate renal impairment; and if the patient has moderate renal impairment, then orally administering once a day to the patient, a dosage form containing a combination of 105 mg or less of bupropion hydrochloride, or a molar equivalent amount of the free base or another salt form of bupropion, and 45 mg or less of dextromethorphan hydrobromide, or a molar equivalent amount of the free base or another salt form of dextromethorphan, wherein the molar ratio of the bupropion to the dextromethorphan is about the ratio of the molar amount of bupropion in 105 mg of bupropion hydrochloride to the molar amount of dextromethorphan in 45 mg of dextromethorphan hydrobromide;

if the patient does not have renal impairment, then orally administering twice a day to the patient, a dosage form containing a combination of 105 mg of bupropion hydrochloride, or a molar equivalent amount of the free base or another salt form of bupropion, and 45 mg of dextromethorphan hydrobromide, or a molar equivalent amount of the free base or another salt form of dextromethorphan;

wherein a risk of somnolence and dizziness for a patient who has moderate renal impairment is lower following orally administering the dosage form containing the combination once a day to the patient than it would be if a combination of 105 mg of bupropion hydrochloride and 45 mg of dextromethorphan hydrobromide were administered twice a day to the patient for the same number of days.

Some embodiments include a method of treating major depressive disorder in a human patient who requires concomitant treatment with a strong CYP2D6 inhibitor, comprising administering, once daily to the human patient, a combination of about 105 mg of bupropion hydrochloride and about 45 mg of dextromethorphan hydrobromide, wherein the human patient is experiencing major depressive disorder and is receiving concomitant treatment with the strong CYP2D6 inhibitor. In some embodiments, the strong CYP2D6 inhibitor is paroxetine.

Some embodiments include a method of treating major depressive disorder in a patient receiving a concomitant strong CYP2D6 inhibitor, comprising administering a daily dose of: (i) about 105 mg of bupropion hydrochloride and (ii) about 45 mg of dextromethorphan hydrobromide to a human patient who has major depressive disorder and is receiving concomitant treatment with a strong CYP2D6 inhibitor.

Some embodiments include a method of treating major depressive disorder in a patient who is a known CYP2D6 poor metabolizer, comprising administering a daily dose of: (i) about 105 mg of bupropion hydrochloride and (ii) about 45 mg of dextromethorphan hydrobromide to a human patient who is experiencing major depressive disorder and is known to be a CYP2D6 poor metabolizer.

Some embodiments include a method of using an N-methyl D-aspartate (NMDA) receptor antagonist to treat major depressive disorder, comprising administering, no more than twice daily, a combination of 105 mg of bupropion hydrochloride and 45 mg of dextromethorphan hydrobromide to a human patient who is experiencing major depressive disorder, wherein the dextromethorphan acts as an uncompetitive antagonist of the NMDA receptor and a sigma-1 receptor agonist, and the human patient does not experience dissociation.

Some embodiments include a method of treating major depressive disorder in a human patient at risk of QT prolongation, comprising administering, no more than twice daily, a combination of 105 mg of bupropion hydrochloride and 45 mg of dextromethorphan hydrobromide to a human patient who is experiencing major depressive disorder and is at risk of QT prolongation and torsades de pointes, wherein electrocardiographic evaluation of QT interval is not conducted on the human patient.

Some embodiments include a method of treating a patient with major depressive disorder, comprising: administering a therapeutically effective amount of a combination of a dextromethorphan and a bupropion, wherein the patient has mild hepatic impairment, defined as Child-Pugh A, or moderate hepatic impairment, defined as Child-Pugh B, and wherein the therapeutically effective amount is the same amount that would be administered to a patient with normal hepatic function.

Some embodiments include a method of treating major depressive disorder, comprising: determining whether a human patient has hepatic impairment; and
if the human patient has mild hepatic impairment, defined as Child-Pugh A, or moderate hepatic impairment, defined as Child-Pugh B, administering twice a day to the human patient, a combination of 45 mg of dextromethorphan hydrobromide and 105 mg of bupropion hydrochloride; and if the human patient has severe hepatic impairment, defined as Child-Pugh C, avoiding use of the combination of 45 mg of dextromethorphan hydrobromide and 105 mg of bupropion hydrochloride on the human patient.

DETAILED DESCRIPTION

As mentioned above, this disclosure relates to administration of a combination of: 1) about 100-110 mg, about 104-106 mg, or about 105 mg of bupropion hydrochloride, or a molar equivalent amount of a free base form or another salt form of dextromethorphan; and 2) about 40-50 mg, about 44-46 mg, or about 45 mg of dextromethorphan hydrobromide, or a molar equivalent amount of a free base form or another salt form of dextromethorphan. This combination is referred to for convenience herein as the "subject combination." In every instance where the subject combination is referred to herein, the combination of 105 mg of bupropion hydrochloride and 45 mg of dextromethorphan hydrobromide is specifically contemplated.

Strong CYP2D6 inhibitors include, but are not limited to, compounds such as fluoxetine, propafenone, quinidine, and paroxetine.

Dextromethorphan hydrobromide is an uncompetitive NMDA receptor antagonist and a sigma-1 receptor agonist.

The chemical name of dextromethorphan hydrobromide is morphinan, 3-methoxy-17-methyl-, (9α, 13α, 14α), hydrobromide monohydrate. Dextromethorphan hydrobromide has the empirical formula $C_{18}H_{25}NO \cdot HBr \cdot H_2O$ and a molecular weight of 370.33. The structural formula is:

Dextromethorphan hydrobromide powder is white or almost white, crystalline, and sparingly soluble in water.

Bupropion hydrochloride is an aminoketone and CYP450 2D6 inhibitor.

The chemical name of bupropion hydrochloride is: (±)-1-(3-chlorophenyl)-2-[(1,1-dimethylethyl)amino]-1-propanone hydrochloride. Bupropion hydrochloride has the empirical formula $C_{13}H_{18}ClNO \cdot HCl$ and a molecular weight of 276.2. The structural formula is:

Bupropion hydrochloride powder is white and highly soluble in water.

The subject combination may be contained in an oral dosage form, including a tablet, such as an extended-release tablet. In some embodiments, the subject combination is contained in a dosage form for oral administration and is available as round bilayer tablets.

In some embodiments, each tablet containing the subject combination contains 45 mg of dextromethorphan hydrobromide in an immediate-release formulation. In some embodiments, each tablet of the subject combination contains 105 mg of bupropion hydrochloride in an extended-release formulation. In some embodiments, each tablet of the subject combination contains 45 mg of dextromethorphan hydrobromide in an immediate-release formulation and 105 mg of bupropion hydrochloride in an extended-release formulation.

In some embodiments, a tablet containing the subject combination contains l-cysteine hydrochloride monohydrate. In some embodiments, a tablet containing the subject combination contains carbomer homopolymer. In some embodiments, a tablet containing the subject combination contains microcrystalline cellulose. In some embodiments, a tablet containing the subject combination contains colloidal silicon dioxide. In some embodiments, a tablet containing the subject combination contains crospovidone. In some embodiments, a tablet containing the subject combination contains stearic acid. In some embodiments, a tablet containing the subject combination contains magnesium stearate.

In some embodiments, a tablet containing the subject combination contains the following inactive ingredients: l-cysteine hydrochloride monohydrate, carbomer homopolymer, microcrystalline cellulose, colloidal silicon dioxide, crospovidone, stearic acid, and magnesium stearate.

In some embodiments, the starting dosage of the subject combination is 45 mg of dextromethorphan hydrobromide and 105 mg of bupropion hydrochloride in one tablet that is administered once daily in the morning. In some embodiments, after 3 days, the dosage is increased to one tablet (or one dosage form containing 45 mg of dextromethorphan hydrobromide and 105 mg of bupropion hydrochloride) twice daily, e.g., given at least 8 hours apart. In some embodiments, no more than two doses containing 45 mg of dextromethorphan hydrobromide and 105 mg of bupropion hydrochloride are administered in the same day.

No dose adjustment is recommended in patients with mild (Child-Pugh A) or moderate hepatic impairment (Child-Pugh B) as compared with the dose recommended to a patient with normal hepatic function.

The pharmacokinetics of the combination of 45 mg of dextromethorphan hydrobromide and 105 mg of bupropion hydrochloride have not been evaluated in patients with severe hepatic impairment (Child-Pugh C). Use of combination of 45 mg of dextromethorphan hydrobromide and 105 mg of bupropion hydrochloride is not recommended, or should be avoided, in patients with severe hepatic impairment.

The subject combination may be administered orally with or without food. In some embodiments, the tablets are swallowed whole, and not crushed, divided, or chewed.

Patients having renal impairment may require special dosing.

In some embodiments, the renal impairment status of the subject may be determined by measuring the "estimated glomerular filtration rate" or "eGFR" of the individual. The eGFR in mL/min/1.73 m² is calculated by the Modification of Diet in Renal Disease [MDRD] equation:

$$\text{(eGFR in mL/min)}/1.73 \text{ m}^2 = 175 \times \text{(serum creatinine in mg/dL)}^{-1.154} \times \text{Age}^{-0.203} \times 0.742 \text{(if female)} \times 1.212 \text{ (if black)}.$$

Further details regarding the calculation of the eGFR may be found in, e.g., Levey A S, Coresh J, Greene T, Marsh J, Stevens L A, Kusek J W, Van Lente F: Chronic Kidney Disease Epidemiology Collaboration. Expressing the Modification of Diet in Renal Disease Study Equation for Estimating Glomerular Filtration Rate with Standardized Serum Creatinine Values. *Ann Intern Med.* 2009; 150(9):604-12.

Renal impairment status based on Food and Drug Administration (FDA) guidance is as follows.
Normal: eGFR≥90 mL/min/1.73 m²
Mild: eGFR 60-89 mL/min/1.73 m2 (i.e., ≥60 to <90)
Moderate: eGFR 30-59 mL/min/1.73 m² (i.e., ≥30 to <60)
Severe: eGFR 15-29 mL/min/1.73 m² (i.e., ≥15 to <30) and not on hemodialysis
End-stage renal disease (ESRD): eGFR<15 mL/min/1.73 m² and not on hemodialysis or on hemodialysis
See, Guidance for Industry Pharmacokinetics in Patients with Impaired Renal Function—Study Design, Data Analysis and Impact on Dosing and Labeling. U.S. Department of Health and Human Services Food and Drug Administration Center for Drug Evaluation and Research (CDER) Center for Biologics Evaluation and Research (CBER) February 2010. As used herein, a "renally impaired subject" may have mild, moderate, or severe renal impairment, or may have ESRD.

In some embodiments, the recommended dosage of the subject combination for patients with moderate renal impairment (estimated glomerular filtration rate (eGFR) or glomerular filtration rate (GFR) of 30 to 59 mL/minute/1.73 m²) is a daily dose of 45 mg of dextromethorphan hydrobromide and 105 mg of bupropion hydrochloride, or a molar equivalent amount of another form of dextromethorphan and/or bupropion, such as administration of one tablet (or one dosage form containing 45 mg of dextromethorphan hydrobromide and 105 mg of bupropion hydrochloride) once daily, such as one tablet or other oral dosage form daily in the morning, or twice daily oral administration of a combination of 52.5 mg of bupropion hydrochloride and about 22.5 mg of dextromethorphan hydrobromide. In some embodiments, the patients are monitored for adverse reactions potentially attributable to dextromethorphan, such as somnolence and dizziness.

Moderate renal impairment may be determined by an assay, such as an assay that determines creatinine levels, on a biological sample from the patient, such as a blood sample. Serum creatinine levels from a blood sample can be used to estimate GFR.

Patients who are concomitantly using the subject combination with strong CYP2D6 inhibitors may require special dosing. Concomitant use of the subject combination with a strong CYP2D6 inhibitor increases plasma concentrations of dextromethorphan. In some embodiments, the recommended dosage of the subject combination when coadministered with a strong CYP2D6 inhibitor is one tablet (or one dosage form containing 45 mg of dextromethorphan hydrobromide and 105 mg of bupropion hydrochloride) once daily, such as one tablet or other oral dosage form daily in the morning. In some embodiments, the patients are monitored for adverse reactions potentially attributable to dextromethorphan, such as somnolence and dizziness.

Patients who are known CYP2D6 poor metabolizers (PMs) may require special dosing. In some embodiments, the recommended dosage for patients known to be poor CYP2D6 metabolizers is one tablet (or one dosage form containing 45 mg of dextromethorphan hydrobromide and 105 mg of bupropion hydrochloride) once daily, such as one tablet or other oral dosage form daily in the morning.

Special precautions may be required when switching a patient to or from a monoamine oxidase inhibitor (MAOI) antidepressant to the subject combination. In some embodiments, at least 14 days must elapse between discontinuation of an MAOI intended to treat depression and initiation of therapy with the subject combination. Conversely, in some embodiments, at least 14 days must be allowed after stopping the subject combination before starting an MAOI antidepressant.

There is data that reports the presence of bupropion and its metabolites in human milk. There is no data on the effects of bupropion or its metabolites on milk production. Limited data related to bupropion use in lactating patients have not identified a clear association of adverse reactions in the breastfed infant.

Neurotoxicity findings were observed in juvenile rats treated with a combination of dextromethorphan/quinidine on postnatal day (PND) 7, which corresponds to the third trimester of gestation through the first few months of life and may extend through the first three years of life in humans. It is not known whether dextromethorphan is present in human milk. There are no data on the effects of dextromethorphan on the breastfed infant or the effects on milk production. Because of the potential for neurotoxicity, in some embodiments, patients should be advised that breastfeeding is not recommended during treatment with a combination of dextromethorphan and bupropion and for 5 days following final dose.

In some embodiments, the human child of a patient receiving the subject combination is at risk of seizure. In some embodiments, the human child is about three years old or younger. In some embodiments, the human child of a patient receiving the subject combination is at risk of neurotoxicity.

For lactating human mothers, the combination of about 45 mg of dextromethorphan hydrobromide and about 105 mg of bupropion hydrochloride may be taken twice daily for about 1 week to about 6 weeks, about 6 weeks, or at least 6 weeks, before stopping the treatment at least 5 days before beginning breastfeeding the child.

In some embodiments, the human patient produces milk that is substantially free of dextromethorphan after 5 days from the final dose of the combination.

In some embodiments, the human patient produces milk that is substantially free of bupropion after 5 days from the final dose of the combination.

In some embodiments, the human child of a patient receiving the subject combination is not exposed to a detectable amount of dextromethorphan during breastfeeding.

In some embodiments, the human child of a patient receiving the subject combination is not exposed to a detectable amount of bupropion during breastfeeding.

In some embodiments, the subject combination is administered to the human patient twice daily until the human patient experiences a reduction from baseline of at least about 7, at least about 11, at least about 13, or at least about 15.9 in the human patient's total MADRS score. When the desired reduction in the MADRS score is reached, the human patient may stop the treatment, wait at least 5 day, and then begin breastfeeding her child.

In some embodiments, the human child is a breastfed infant.

In some embodiments, the human patient experiences a reduction from baseline in total MADRS score in the human patient for administering the subject combination that is more than the patient would experience if a placebo were administered. The human patient taking the subject combination may experience the greater reduction in MADRS score than taking a placebo at, for example, after 1 week of administration, after 2 weeks of administration, after 3 weeks of administration, after 4 weeks of administration, after 5 weeks of administration, after 6 weeks of administration, or at other times.

In the subject combination, bupropion inhibits the metabolism of dextromethorphan via CYP2D6. Dextromethorphan, when co-administered with bupropion, displays nonlinear pharmacokinetics at steady state, with greater than dose-proportional changes in AUC and $C_{max}$ for varying doses of dextromethorphan (30 to 60 mg) and less than dose-proportional changes for varying doses of bupropion (75 to 150 mg).

Steady state plasma concentrations of dextromethorphan and bupropion when given as the subject combination are achieved within 8 days. The accumulation ratios for dextromethorphan at steady state are about 20 and about 32, respectively based on $C_{max}$ and $AUC_{0-12}$. The accumulation ratios for bupropion at steady state are 1.1 and 1.5, respectively based on $C_{max}$ and $AUC_{0-12}$.

After administration of the subject combination, the median $T_{max}$ of dextromethorphan is about 3 hours and the median $T_{max}$ of bupropion is about 2 hours. The $C_{max}$ of hydroxybupropion metabolite occurs approximately 3 hours post-dose and is approximately 14 times the peak level of bupropion. The $AUC_{0-12}$ hydroxybupropion is about 19 times that of bupropion. The $C_{max}$ of the erythrohydroxybupropion and threohydroxybupropion metabolites occurs approximately 4 hours post-dose and is approximately equal to and about 5 times that of bupropion, respectively. The $AUC_{0-12}$ values of erythrohydroxybupropion and threohydroxybupropion are about 1.2 and about 7 times that of bupropion, respectively.

The subject combination can be taken with or without food. Dextromethorphan $C_{max}$ and $AUC_{0-12}$ were unchanged and decreased by 14%, respectively, and bupropion $C_{max}$ and $AUC_{0-12}$ were increased by 3% and 6%, respectively, when the subject combination was administered with food.

The plasma protein binding of dextromethorphan is approximately 60-70% and bupropion is 84%. The extent of protein binding of the hydroxybupropion metabolite is similar to that for bupropion; whereas the extent of protein binding of the threohydroxybupropion metabolite is about half that seen with bupropion.

Following 8 days of administration of the subject combination in extensive metabolizers, the mean elimination half-life of dextromethorphan was increased approximately 3-fold to about 22 hours, as compared to dextromethorphan given without bupropion.

The mean elimination half-life of dextromethorphan and bupropion was 22 hours and hours, respectively. The apparent elimination half-life of hydroxybupropion, erythrohydroxybupropion and threohydroxybupropion metabolites were approximately 35, 44 and 33 hours, respectively.

Esketamine is a non-competitive NMDA receptor antagonist indicated, in conjunction with an oral antidepressant, for the treatment of treatment-resistant depression in adults. Treatment of treatment-resistant depression carries a risk of dissociation. The label for esketamine states that because of the risks of sedation and dissociation, patients must be monitored for at least 2 hours at each treatment session, followed by an assessment to determine when the patient is considered clinically stable and ready to leave the healthcare setting.

Dissociation includes: delusional perception; depersonalization/derealization disorder; derealization; diplopia; dissociation; dysesthesia; feeling cold; feeling hot; feeling of body temperature change; hallucination; hallucination, auditory; hallucination, visual; hyperacusis; illusion; ocular discomfort; oral dysesthesia; paranesthesia; paranesthesia oral; pharyngeal paranesthesia; photophobia; time perception altered; tinnitus; vision blurred; visual impairment.

The subject combination is a combination of dextromethorphan, an uncompetitive N-methyl D-aspartate (NDMA) receptor antagonist and sigma-1 receptor agonist, and bupropion, an aminoketone and CYP450 2D6 inhibitor, indicated for the treatment of major depressive disorder (MDD) in adults. Unlike esketamine, the subject combination can be administered as a without dissociation or dissociative events. In some embodiments, the patient is not monitored for dissociation after the subject combination is administered.

The following information includes the kinds of dissociative and other effects that may be avoided with the combination of dextromethorphan and bupropion.

In clinical trials, 48% to 61% of esketamine-treated patients developed sedation based on the Modified Observer's Assessment of Alertness/Sedation scale (MOAA/S), and 0.3% to 0.4% of esketamine-treated patients experienced loss of consciousness (MOAA/S score of 0). For a combination of dextromethorphan and bupropion, NMDA receptor antagonism may be achieved without a significant risk of sedation.

Because of the possibility of delayed or prolonged sedation, patients receiving esketamine must be monitored by a healthcare provider for at least 2 hours at each treatment session, followed by an assessment to determine when the patient is considered clinically stable and ready to leave the healthcare setting. No such monitoring is required for the treatment of the subject combination of dextromethorphan and bupropion.

Esketamine-treated patients must be closely monitored for sedation with concomitant use of ESKETAMINE with CNS depressants. No such monitoring is required for the treatment of the subject combination of dextromethorphan and bupropion.

Esketamine is available only through a restricted program under a Risk Evaluation and Mitigation Strategy (REMS). No such restrictions are required for the subject combination of dextromethorphan and bupropion.

The most common psychological effects of esketamine were dissociative and/or perceptual changes (including distortion of time, space and illusions), derealization and depersonalization (61% to 84% of esketamine-treated patients developed dissociative or perceptual changes based on the Clinician-Administered Dissociative States Scale). Given its potential to induce dissociative effects, patients with psychosis must be carefully assessed before administering esketamine. No such assessment is required for the treatment of the subject combination of dextromethorphan and bupropion. Treatment with esketamine should be initiated only if the benefit outweighs the risk. No such restriction is required with the treatment of the subject combination of dextromethorphan and bupropion.

Because of the risks of dissociation, patients receiving esketamine must be monitored by a healthcare provider for at least 2 hours at each treatment session, followed by an assessment to determine when the patient is considered clinically stable and ready to leave the healthcare setting. No such monitoring, assessment, or restriction is required for the treatment of the subject combination of dextromethorphan and bupropion.

Dissociation includes: delusional perception (including distortion of space and time, and illusions); depersonalization/derealization disorder; derealization; diplopia; dissociation; dysesthesia; feeling cold; feeling hot; feeling of body temperature change; hallucination; hallucination, auditory; hallucination, visual; hallucinations, mixed; hyperacusis; illusion; ocular discomfort; oral dysesthesia; paresthesia; paresthesia oral; pharyngeal paresthesia; photophobia; time perception altered; tinnitus; vision blurred; and visual impairment.

Esketamine is a Schedule Ill controlled substance (CIII), and may be subject to abuse and diversion. The subject combination of dextromethorphan and bupropion is not a controlled substance. Each patient's risk for abuse or misuse must be assessed prior to prescribing and all patients receiving esketamine must be monitored for the development of these behaviors or conditions, including drug-seeking behavior, while on therapy. No such monitoring or assessment is required for the treatment of the subject combination of dextromethorphan and bupropion.

Esketamine is available only through a restricted program under a Risk Evaluation and Mitigation Strategy (REMS) and is called the esketamine REMS because of the risks of serious adverse outcomes from sedation, dissociation, and abuse and misuse. No such restrictions are required for the subject combination of dextromethorphan and bupropion.

Important requirements of the esketamine REMS include the following:
  Healthcare settings must be certified in the program and ensure that esketamine is:
    Only dispensed and administered in healthcare settings.
    Patients treated in outpatient settings (e.g. medical offices and clinics) must be enrolled in the program.
    Administered by patients under the direct observation of a healthcare provider and that patients are monitored by a healthcare provider for at least 2 hours after administration of esketamine.
None of these requirements apply to the subject combination of dextromethorphan and bupropion.

Esketamine was evaluated for safety in 262 adults for the treatment of depressive symptoms in adults with major depressive disorder (MDD) with acute suicidal ideation or behavior from two Phase 3 studies (Study 3 and Study 4) and one Phase 2 study.

Sedation was evaluated by adverse event reports and the Modified Observer's Assessment of Alertness/Sedation (MOAA/S). In the MOAA/S, a score of 5 means "responds readily to name spoken in normal tone;" a score of 0 means "no response after painful trapezius squeeze;" a score of 4 means "lethargic response to name spoken in normal tone;" a score of 3 means "responds only after name is spoken loudly and/or repeatedly;" a score of 2 means "responds only after mild prodding or shaking;" and a score of 1 means "dose not respond to mild prodding or shaking." Any decrease in MOAA/S score from pre-dose is considered to indicate the presence of sedation, and such a decrease occurred in a higher number of patients on esketamine than placebo during the short-term Treatment Resistant Depression (TRD) studies. Dose-related increases in the incidence of sedation (MOAA/S score<5) were observed in a fixed-dose TRD study. Table 1 presents the incidence of sedation (MOAA/S score<5) in a fixed-dose study with adult patients <65 years of age with TRD and a flexible-dose study with patients 65 years of age with TRD.

TABLE 1

Incidence of Sedation (MOAA/S Score <5) in Double-Blind, Randomized, Placebo-Controlled Studies (Fixed-Dose Study with Adult Patients <65 Years of Age with treatment-resistant depression and Flexible-Dose Study with Patients ≥65 Years of Age with treatment-resistant depression)

|  | Patients <65 years | | | Patients ≥65 years | |
| --- | --- | --- | --- | --- | --- |
|  | Placebo + Oral AD | SPRAVATO + Oral AD | | Placebo + Oral AD | SPRAVATO + Oral AD |
|  |  | 56 mg | 84 mg |  | 28 to 84 mg |
| Number of patients* | N = 112 | N = 114 | N = 114 | N = 63 | N = 72 |
| Sedation (MOAA/S score <5) | 119% | 50% | 61% | 19% | 49% |

*Patients who were evaluated with MOAA/S

In studies for the treatment of depressive symptoms in adults with MDD with acute suicidal ideation or behavior, there was a higher incidence of sedation (MOAA/S score<5) in patients treated with esketamine plus oral antidepressant compared to patients treated with placebo plus oral antidepressant (AD), similar to the treatment-resistant depression study results in Table 1.

Dissociation/Perceptual Changes Esketamine can cause dissociative symptoms (including derealization and depersonalization) and perceptual changes (including distortion of time and space, and illusions). In clinical trials, dissociation was transient and occurred on the day of dosing.

Dissociation was evaluated by adverse event reports and the Clinician-Administered Dissociative States Scale (CADSS). A CADSS total score of more than 4 indicates the presence of dissociative symptoms, and such an increase to a score of 4 or more occurred in a higher number of patients on esketamine compared to placebo during the short-term treatment-resistant depression studies. Dose-related increases in the incidence of dissociative symptoms (CADSS total score>4 and change>0) were observed in a fixed-dose treatment-resistant depression study. Table 2 presents the incidence of dissociation (CADSS total score>4 and change>0) in a fixed-dose study with adult patients <65 years of age with treatment-resistant depression and a flexible-dose study with patients ≥65 years of age with treatment-resistant depression.

TABLE 2

Incidence of Dissociation (CADSS Total Score >4 and Change >0) in Double-Blind, Randomized, Placebo-Controlled Studies (Fixed-Dose Study with Adult Patients <65 Years of Age with treatment-resistant depression and Flexible-Dose Study with Patients ≥65 Years of Age with treatment-resistant depression)

|  | Patients <65 years | | | Patients ≥65 years | |
| --- | --- | --- | --- | --- | --- |
|  | Placebo + Oral AD | ESKETAMINE + Oral AD | | Placebo + Oral AD | ESKETAMINE + Oral AD |
|  |  | 56 mg | 84 mg |  | 28 to 84 mg |
| Number of patients* | N = 113 | N = 113 | N = 116 | N = 65 | N = 72 |
| CADSS total score >4 and change >0 | 5% | 61% | 69% | 12% | 75% |

*Number of patients who were evaluated with CADSS

In studies for the treatment of depressive symptoms in adults with MDD with acute suicidal ideation or behavior, patients treated with esketamine plus oral AD also demonstrated a higher percentage (84%) of patients with dissociation (CADSS total score>4 and change>0) compared to patients treated with placebo plus oral AD (16%).

Because the subject combination can be administered without dissociation or dissociative events, its risk of abuse is reduced as compared to esketamine. Abuse is the intentional, non-therapeutic use of a drug, even once, for its desirable psychological or physiological effects. Clinical studies with the subject combination of dextromethorphan and bupropion did not reveal drug-seeking behavior, although these observations were not systematic. Therefore, patients with a history of drug abuse may be observed closely for signs of the subject combination of dextromethorphan and bupropion misuse or abuse (e.g., development of tolerance, increases in dose, drug-seeking behavior).

Unlike the combination of quinidine and dextromethorphan, at a dose of a combination of 105 mg of bupropion hydrochloride and 45 mg of dextromethorphan hydrobromide given twice a day, the subject combination does not prolong the QT interval to any clinically relevant extent. Thus, for a human patient who is experiencing major depressive disorder and is at risk of QT prolongation and torsades de pointes, electrocardiographic evaluation of QT interval is not typically conducted on the human patient.

The subject combination may be used for adjunctive treatment of major depressive disorder or depression.

In addition to major depressive disorder, the subject combination may be used to treat other diseases in conditions in the patient populations or circumstances described herein. For example, the subject combination may be used to treat pain or a neurological disorder. Examples of neurological disorders that may be treated with the subject combination include, but are not limited to: affective disorders, psychiatric disorders, cerebral function disorders, movement disorders, dementias, motor neuron diseases, neurodegenerative diseases, seizure disorders, and headaches.

Affective disorders that may be treated by the subject combination include, but are not limited to, depression, major depression, treatment resistant depression, treatment resistant bipolar depression, bipolar disorders including cyclothymia, seasonal affective disorder, mood disorders, chronic depression (dysthymia), psychotic depression, postpartum depression, premenstrual dysphoric disorder (PMDD), situational depression, atypical depression, mania, anxiety disorders, attention deficit disorder (ADD), attention deficit disorder with hyperactivity (ADDH), and attention deficit/hyperactivity disorder (AD/HD), bipolar and manic conditions, obsessive-compulsive disorder, bulimia, obesity or weight-gain, narcolepsy, chronic fatigue syndrome, premenstrual syndrome, substance addiction or abuse, nicotine addiction, psycho-sexual dysfunction, pseudobulbar affect, and emotional lability.

Depression may be manifested by depressive symptoms. These symptoms may include psychological changes such as changes in mood, feelings of intense sadness, despair, mental slowing, loss of concentration, pessimistic worry, agitation, anxiety, irritability, guilt, anger, feelings of worthlessness, reckless behavior, suicidal thoughts, or attempts, and/or self-deprecation. Physical symptoms of depression may include insomnia, anorexia, appetite loss, weight loss, weight gain, decreased energy and libido, fatigue, restlessness, aches, pains, headaches, cramps, digestive issues, and/or abnormal hormonal circadian rhythms.

Psychiatric disorders that may be treated by the subject combination, include, but are not limited to, anxiety disorders, including but not limited to, phobias, generalized anxiety disorder, social anxiety disorder, panic disorder, agoraphobia, obsessive-compulsive disorder, and post-traumatic stress disorder (PTSD); mania, manic depressive illness, hypomania, unipolar depression, depression, stress disorders, somatoform disorders, personality disorders, psychosis, schizophrenia, delusional disorder, schizoaffective disorder, schizotypy, aggression, aggression in Alzheimer's disease, agitation, and agitation in Alzheimer's disease. Alzheimer's disease may also be referred to as dementia of the Alzheimer's type. Other neurobehavioral symptoms of Alzheimer's disease that may be treated include disinhibition and apathy.

Agitation in Alzheimer's disease occurs as the disease progresses. Agitation may present itself as inappropriate verbal, emotional, and/or physical behaviors. Inappropriate behaviors may include, but are not limited to, incoherent babbling, inappropriate emotional response, demands for attention, threats, irritability, frustration, screaming, repetitive questions, mood swings, cursing, abusive language, physical outbursts, emotional distress, restlessness, shredding, sleeping disturbances, delusions, hallucinations, pacing, wandering, searching, rummaging, repetitive body motions, hoarding, shadowing, hitting, scratching, biting, combativeness, hyperactivity, and/or kicking.

Alzheimer's disease (AD) is a progressive neurodegenerative disorder characterized by cognitive decline, and behavioral and psychological symptoms including agitation. AD is the most common form of dementia and afflicts an estimated 6 million individuals in the United States, a number that is anticipated to increase to approximately 14 million by 2050. Agitation is reported in up to 70% of patients with AD and is characterized by emotional distress, aggressive behaviors, disruptive irritability, and disinhibition. Managing agitation is a priority in AD. Agitation in patients with AD has been associated with increased caregiver burden, decreased functioning, accelerated cognitive decline, earlier nursing home placement, and increased mortality. There are currently no therapies approved by the FDA for the treatment of agitation in patients with AD.

Neurobehavioral symptoms have been known to appear during dementia and may be treated by the combination. Caregivers or families may feel more overwhelmed by patients' behavioral/psychological symptoms than by their cognitive impairment. Common forms of the syndrome are Alzheimer's disease, vascular dementia, dementia with Lewy bodies (abnormal aggregates of protein that develop inside nerve cells), and a group of diseases that contribute to frontotemporal dementia (degeneration of the frontal lobe of the brain). The symptoms that dementia patients have are similar to those of psychiatric disorders, but some are slightly different from each other. Neurobehavioral symptoms associated with dementia include depression, apathy, agitation, disinhibition, hallucinations, delusions, psychosis, impulsiveness, aggressiveness, compulsion, excessive sex drive, and personality disorders. Neurobehavioral symptoms such as disinhibition may also be found in other conditions such as traumatic brain injury.

Agitation in patients with Alzheimer's disease may be assessed using the Cohen Mansfield Agitation Inventory or CMAI. The CMAI assesses various behaviors including, Hitting (including self), Kicking, Grabbing onto people, Pushing, Throwing things, Biting, Scratching, Spitting, Hurting self or others, Tearing things or destroying property, Making physical sexual advances, Pacing, aimless wandering, Inappropriate dress or disrobing, Trying to get to a different place, Intentional falling, Eating/drinking inappropriate substances, Handling things inappropriately, Hiding things, Hoarding things, Performing repetitive mannerisms, General restlessness, Screaming, Making verbal sexual advances, Cursing or verbal aggression, Repetitive sentences or questions, Strange noises (weird laughter or crying), Complaining, Negativism, Constant unwarranted request for attention or help.

Schizophrenia may be treated by the combination including positive symptoms and/or negative symptoms of schizophrenia, or residual symptoms of schizophrenia. Other conditions that may treated include intermittent explosive disorder.

Cerebral function disorders that may be treated by the subject combination include, but are not limited to, disorders involving intellectual deficits such as senile dementia, Alzheimer's type dementia, memory loss, amnesia/amnestic syndrome, epilepsy, disturbances of consciousness, coma, lowering of attention, speech disorders, voice spasms, Parkinson's disease, Lennox-Gastaut syndrome, autism, hyperkinetic syndrome, and schizophrenia. Cerebral function disorders also include disorders caused by cerebrovascular diseases including, but not limited to, stroke, cerebral infarction, cerebral bleeding, cerebral arteriosclerosis, cerebral venous thrombosis, head injuries, and the like where symptoms include disturbance of consciousness, senile dementia, coma, lowering of attention, and speech disorders.

Substance addiction abuse that may be treated by the subject combination includes, but is not limited to, drug dependence, addiction to cocaine, psychostimulants (e.g., crack, cocaine, speed, meth), nicotine, alcohol, opioids, anxiolytic and hypnotic drugs, *cannabis* (marijuana), amphetamines, hallucinogens, phencyclidine, volatile solvents, and volatile nitrites. Nicotine addiction includes nicotine addiction of all known forms, such as smoking cigarettes, cigars and/or pipes, e-cigarettes or vaping, and addiction to chewing tobacco.

Movement disorders that may be treated by the subject combination include, but are not limited to, akathisia, akinesia, associated movements, athetosis, ataxia, ballismus, hemiballismus, bradykinesia, cerebral palsy, chorea, Huntington's disease, Huntington's disease chorea, rheumatic chorea, Sydenham's chorea, dyskinesia, tardive dyskinesia, dystonia, blepharospasm, spasmodic torticollis, dopamine-responsive dystonia, Parkinson's disease, restless legs syndrome (RLS), tremor, essential tremor, and Tourette's syndrome, and Wilson's disease.

Dementias that may be treated by the subject combination include, but are not limited to, Alzheimer's disease, Parkinson's disease, vascular dementia, dementia with Lewy bodies, mixed dementia, fronto-temporal dementia, Creutzfeldt-Jakob disease, normal pressure hydrocephalus, Huntington's disease, Wernicke-Korsakoff Syndrome, and Pick's disease.

Motor neuron diseases that may be treated by the subject combination include, but are not limited to, amyotrophic lateral sclerosis (ALS), progressive bulbar palsy, primary lateral sclerosis (PLS), progressive muscular atrophy, post-polio syndrome (PPS), spinal muscular atrophy (SMA), spinal motor atrophies, Tay-Sach's disease, Sandoff disease, and hereditary spastic paraplegia.

Neurodegenerative diseases that may be treated the subject combination include, but are not limited to, Alzheimer's disease, prion-related diseases, cerebellar ataxia, spinocerebellar ataxia (SCA), spinal muscular atrophy (SMA), bulbar muscular atrophy, Friedrich's ataxia, Huntington's disease, Lewy body disease, Parkinson's disease, amyotrophic lateral sclerosis (ALS or Lou Gehrig's disease), multiple sclerosis (MS), multiple system atrophy, Shy-Drager syndrome, corticobasal degeneration, progressive supranuclear palsy, Wilson's disease, Menkes disease, adrenoleukodystrophy, cerebral autosomal dominant arteriopathy with subcortical infarcts and leukoencephalopathy (CADASIL), muscular dystrophies, Charcot-Marie-Tooth disease (CMT), familial spastic paraparesis, neurofibromatosis, olivopontine cerebellar atrophy or degeneration, striatonigral degeneration, Guillain-Barre syndrome, and spastic paraplesia.

Seizure disorders that may be treated by the subject combination include, but are not limited to, epileptic seizures, nonepileptic seizures, epilepsy, febrile seizures; partial seizures including, but not limited to, simple partial seizures, Jacksonian seizures, complex partial seizures, and epilepsia partialis continua; generalized seizures including, but not limited to, generalized tonic-clonic seizures, absence seizures, atonic seizures, myoclonic seizures, juvenile myoclonic seizures, and infantile spasms; and status epilepticus.

Types of headaches that may be treated by the subject combination include, but are not limited to, migraine, tension, and cluster headaches.

Other neurological disorders that may be treated by the subject combination include, Rett Syndrome, autism, tinnitus, disturbances of consciousness disorders, sexual dysfunction, intractable coughing, narcolepsy, cataplexy; voice disorders due to uncontrolled laryngeal muscle spasms, including, but not limited to, abductor spasmodic dysphonia, adductor spasmodic dysphonia, muscular tension dysphonia, and vocal tremor; diabetic neuropathy, chemotherapy-induced neurotoxicity, such as methotrexate neurotoxicity; incontinence including, but not limited, stress urinary incontinence, urge urinary incontinence, and fecal incontinence; and erectile dysfunction.

In some embodiments, the subject combination may be used to treat pain, joint pain, pain associated with sickle cell disease, pseudobulbar affect, depression (including treatment resistant depression), disorders related to memory and cognition, schizophrenia, Parkinson's disease, amyotrophic lateral sclerosis (ALS), Rhett's syndrome, seizures, cough (including chronic cough), etc.

In some embodiments, the subject combination may be administered orally to relieve musculoskeletal pain including low back pain, and pain associated with rheumatoid arthritis, juvenile rheumatoid arthritis, osteoarthritis, erosive osteoarthritis, sero-negative (non-rheumatoid) arthropathies, non-articular rheumatism, peri-articular disorders, axial spondyloarthritis including ankylosing spondylitis, Paget's disease, fibrous dysplasia, SAPHO syndrome, transient osteoarthritis of the hip, vertebral crush fractures, osteoporosis, etc.

In some embodiments, the subject combination may be administered to relieve inflammatory pain including musculoskeletal pain, arthritis pain, and complex regional pain syndrome.

Arthritis refers to inflammatory joint diseases that can be associated with pain. Examples of arthritis pain include pain associated with osteoarthritis, erosive osteoarthritis, rheumatoid arthritis, juvenile rheumatoid arthritis, sero-negative (non-rheumatoid) arthropathies, non-articular rheumatism, peri-articular disorders, neuropathic arthropathies including Charcot's foot, axial spondyloarthritis including ankylosing spondylitis, and SAPHO syndrome.

In some embodiments, the subject combination is used to treat chronic musculoskeletal pain.

In some embodiments, the subject composition may be administered to relieve complex regional pain syndrome, such as complex regional pain syndrome type I (CRPS-1), complex regional pain syndrome type II (CRPS-II), CRPS-NOS, or another type of CRPS. CRPS is a type of inflammatory pain. CRPS can also have a neuropathic component. Complex regional pain syndrome is a debilitating pain syndrome. It is characterized by severe pain in a limb that can be accompanied by edema, and autonomic, motor, and sensory changes.

In some embodiments, the subject composition may be administered orally to relieve neuropathic pain.

Examples of neuropathic pain include pain due to diabetic peripheral neuropathy or diabetic peripheral neuropathic pain, post-herpetic neuralgia, trigeminal neuralgia, monoradiculopathies, phantom limb pain, central pain, pain due to multiple sclerosis, etc. Other causes of neuropathic pain include cancer-related pain, lumbar nerve root compression, spinal cord injury, post-stroke pain, central multiple sclerosis pain, HIV-associated neuropathy, and radio- or chemotherapy associated neuropathy, etc.

In some embodiments, the subject composition may be administered to relieve fibromyalgia.

In some embodiments, the subject composition may be co-administered with one or more strong Inhibitors of CYP2D6. It has been found that the concomitant use of the subject combination with one or more strong CYP2D6 inhibitors increases plasma concentrations of dextromethorphan. It is thus recommended to monitor patients for adverse effects or adverse reactions potentially attributable to dextromethorphan, such as somnolence and dizziness.

The dosage adjustment may be necessary when the subject composition is co-administered with one or more strong inhibitors of CYP2D6. Adjusting to a lower dose amount of the bupropion and/or the dextromethorphan in the subject combination or less frequent dosing of the subject combination may reduce adverse effects or adverse reactions, such as, but not limited to, somnolence, dizziness, or a combination thereof in a patient. For example, a recommended dosage of the subject combination when co-administered with one or more strong CYP2D6 inhibitors, is one tablet containing 45 mg or less of dextromethorphan hydrobromide and 105 mg or less of bupropion hydrochloride once daily, such as once daily in the morning.

Administration of the subject combination once a day to patients who are receiving a concomitant strong CYP2D6 inhibitor may reduce the adverse effects, such as, but not limited to, somnolence, dizziness, or a combination thereof, as compared to administration of the subject combination twice a day for the same number of days. In some embodiments, reducing the dose amount or dose frequency of the subject combination may reduce somnolence. In some embodiments, reducing the dose amount or dose frequency may reduce dizziness. As dizziness may link to falls, adjusting the dosage to lower amount or lower dose frequency of the subject combination may reduce the risk of falls for a patient taking the subject combination. For example, taking the subject combination once a day may reduce the risk of falls for a patient as compared to taking the subject combination twice a day for the same number of days. This may be important, for example, to elderly patients or patients suffering from a dementia, such as Alzheimer's disease.

In some embodiments, the subject composition may be administered to a patient who has moderate renal impairment. As explained herein, it has been found that administering the subject composition to CYP2D6 poor metabolizers increases plasma concentrations of dextromethorphan as compared to patients who are not CYP2D6 poor metabolizers. It is thus recommended to monitor patients for adverse effects or adverse reactions potentially attributable to dextromethorphan, such as somnolence and dizziness.

Dosage adjustment may be necessary when the patient has moderate renal impairment. Adjusting to a lower dose amount of the bupropion and/or the dextromethorphan in the subject combination or less frequent dosing of the subject combination may reduce adverse effects or adverse reactions, or a risk of adverse effects or adverse reactions, such as, but not limited to, somnolence, dizziness, or a combination thereof in a patient. For example, a recommended dosage of the subject combination when administered to a patient who has moderate renal impairment, is one tablet containing 45 mg or less of dextromethorphan hydrobromide and 105 mg or less of bupropion hydrochloride once daily, such as once daily in the morning.

Administration of the subject combination once a day to patients who have moderate renal impairment may reduce the adverse effects, or the risk of adverse effects, such as, but not limited to, somnolence, dizziness, or a combination thereof, as compared to administration of the subject combination twice a day for same number of days. In some embodiments, reducing the dose amount or dose frequency of the subject combination may reduce somnolence. In some embodiments, reducing dose amount or dose frequency may reduce dizziness. As dizziness may link to falls, adjusting the dosage to lower amount or lower dose frequency of the subject combination may reduce the risk of falls for a patient taking the subject combination. For example, taking the subject combination once a day may reduce the risk of falls for a patient as compared to taking the subject combination twice a day for same number of days. This may be important, for example, to elderly patients or patients suffering from a dementia, such as Alzheimer's disease.

Because the risk of seizure with bupropion is dose-related, in some embodiments, patients are screened for use of other bupropion-containing products prior to initiating treatment with a subject combination. In some embodiments, if concomitant use of a subject combination with other bupropion-containing products is clinically warranted, patients should be informed of the risk. In some embodiments, treatment with a subject combination is discontinued and not restarted if the patient experiences a seizure.

In some embodiments, prior to initiating treatment with a subject combination, patients are screened for use of other dextromethorphan-containing products. In some embodiments, if concomitant use of a subject combination with other serotonergic drugs is clinically warranted, patients are informed of the increased risk for serotonin syndrome and monitored for symptoms. In some embodiments, treatment with a subject combination and/or treatment with the concomitant serotonergic drug is immediately discontinued if the above symptoms occur. In some embodiments, if the above symptoms occur, supportive symptomatic treatment is initiated.

In some embodiments, because the risks of neuropsychiatric reactions are dose-related, patients are screened for use of other bupropion- or dextromethorphan-containing products prior to initiating the subject combination. In some embodiments, if concomitant use of the subject combination with other bupropion- or dextromethorphan-containing products is clinically warranted, patients are monitored for neuropsychiatric reactions and patients are instructed to contact a healthcare provider if such reactions occur.

In some embodiments, the subject combination can increase blood pressure and cause hypertension. In some embodiments, blood pressure is assessed before initiating treatment and is monitored periodically during treatment.

In some embodiments, patients are screened for a personal or family history of bipolar disorder, mania, or hypomania.

The term "treating" or "treatment" includes the diagnosis, cure, mitigation, treatment, or prevention of disease in man or other animals, or any activity that otherwise affects the structure or any function of the body of man or other animals.

A subject combination may be used to treat any disease or condition identified as treatable by the combination of bupropion and dextromethorphan in any of the following U.S. Pat. Nos. 8,569,328, 9,168,234, 9,189,905 9,205,083, 9,238,032, 9,278,095, 9,314,462, 9,370,513, 9,375,429, 9,408,815, 9,421,176, 9,457,023, 9,457,025, 9,474,731, 9,486,450, 9,700,528, 9,700,553, 9,707,191, 9,763,932, 9,861,595, 9,867,819, 9,968,568, 10,058,518, 10,064,857, 10,080,727, 10,092,560, 10,092,561, 10,105,327, 10,105,361, 10,251,879, 10,463,634, 10,512,643, 10,548,857, 10,596,167, 10,772,850, 10,780,064, 10,780,066, 10,786,469, 10,786,496, 10,799,497, 10,806,710, 10,864,209, 10,874,663, 10,874,664, 10,874,665, 10,881,624, 10,881,657, 10,894,046, 10,894,047, 10,898,453, all of which are incorporated by reference herein in their entireties for their disclosure of diseases that may be treated by a combination of bupropion and dextromethorphan, including specific embodiments and combinations described therein.

The following U.S. Provisional applications are also incorporated by reference herein in their entireties: Ser. No. 63/359,143, filed Jul. 7, 2022, Ser. No. 63/370,592, filed Aug. 5, 2022, Ser. No. 63/396,182, filed Aug. 8, 2022, Ser. No. 63/373,040, filed Aug. 19, 2022, and Ser. No. 63/401,541, filed Aug. 26, 2022.

Example 1

In a study of the subject combination in 7 subjects with moderate (GFR 30-60 mL/min) renal impairment compared to 6 matched controls with normal renal function (matched in gender, age, and weight range to impaired subjects), both dextromethorphan and bupropion exposures increased by approximately 2-fold and clearances were reduced by 50%.

Example 2

Approximately 7% to 10% of Caucasians and 3% to 8% of African Americans lack the capacity to metabolize CYP2D6 substrates and are classified as poor metabolizers. In 3 poor metabolizers the pharmacokinetics of the subject combination resulted in an approximate 3-fold and 3.4-fold increase in dextromethorphan $C_{max}$ and $AUC_{0-12}$, respectively, compared to extensive metabolizers. An exploration of steady state pharmacokinetic data in 12 poor metabolizers treated with the subject combination in efficacy trials showed plasma concentrations of dextromethorphan that were generally higher than exposures for non-poor metabolizers.

Example 3

Co-administration of the SSRI paroxetine and the subject combination comprising dextromethorphan and bupropion was studied in 29 healthy volunteers. Paroxetine increased the overall exposure of dextromethorphan by 2.5-fold and had no effect on bupropion. The overall exposure of paroxetine was increased by 1.2-fold when co-administered with the subject combination. Based on these results, when the subject combination is prescribed with drugs that inhibit CYP2D6, the subject combination should be dosed once daily. Use caution when administering the subject combination in conjunction with drugs which are extensively metabolized via CYP2D6.

Example 4

Tablets are prepared for oral administration. They are round bilayer tablets. Each tablet contains 45 mg dextromethorphan hydrobromide (equivalent to 32.98 mg of the dextromethorphan free base) in an immediate-release formulation and 105 mg bupropion hydrochloride (equivalent to 91.14 mg of the bupropion free base) in an extended-release formulation. Each tablet contains the following inactive ingredients: carbomer homopolymer, colloidal silicon dioxide, crospovidone, glyceryl monocaprylocaprate, L-cysteine hydrochloride monohydrate, magnesium stearate, microcrystalline cellulose, polyvinyl alcohol, red iron oxide, sodium lauryl sulfate, stearic acid, talc, titanium dioxide, and/or yellow iron oxide.

Example 5

The properties of the tablets of Example 4, containing a combination of dextromethorphan hydrobromide, which is an uncompetitive NMDA receptor antagonist and sigma-1 receptor agonist, and bupropion hydrochloride, which is an aminoketone and CYP450 2D6 inhibitor, were studied.

Figure 1:
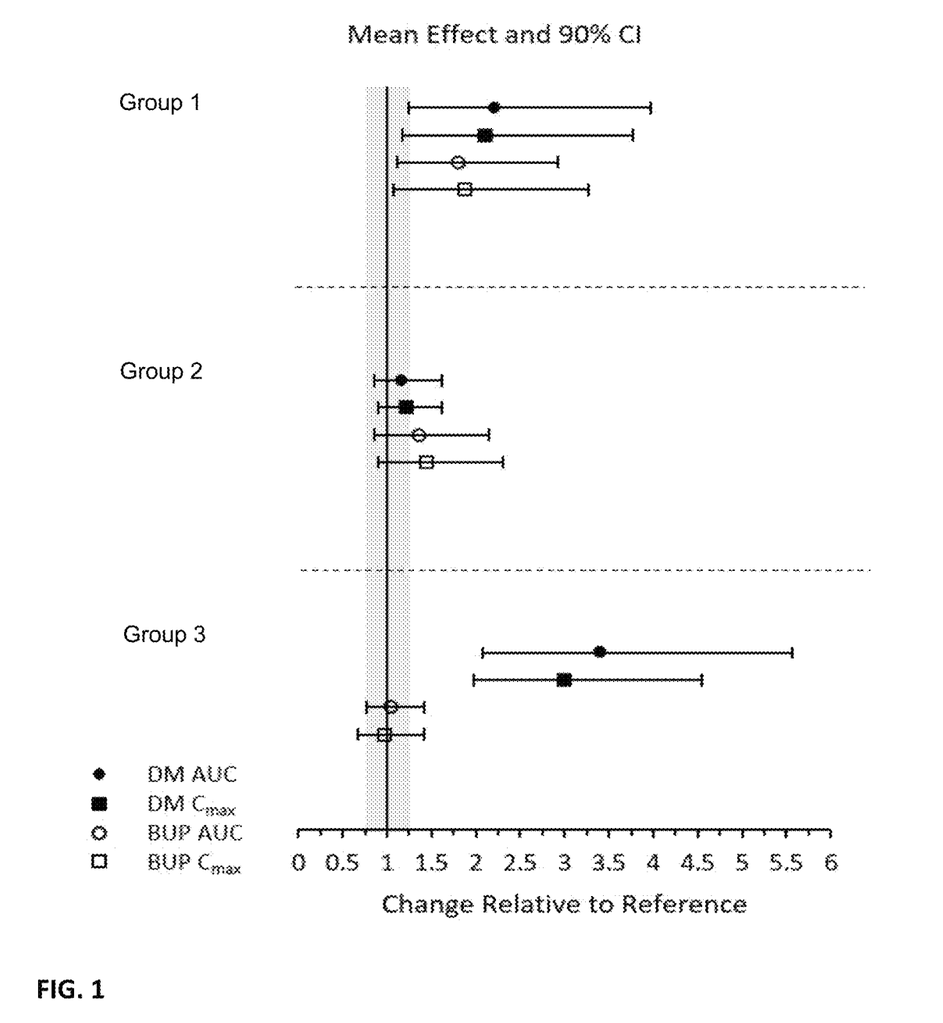
FIG. 1 depicts the effects of renal impairment, hepatic impairment, and CYP2D6 poor metabolizer status on the pharmacokinetics of a tablet containing 45 mg of dextromethorphan hydrobromide and 105 mg of bupropion hydrochloride.
Figure 2:
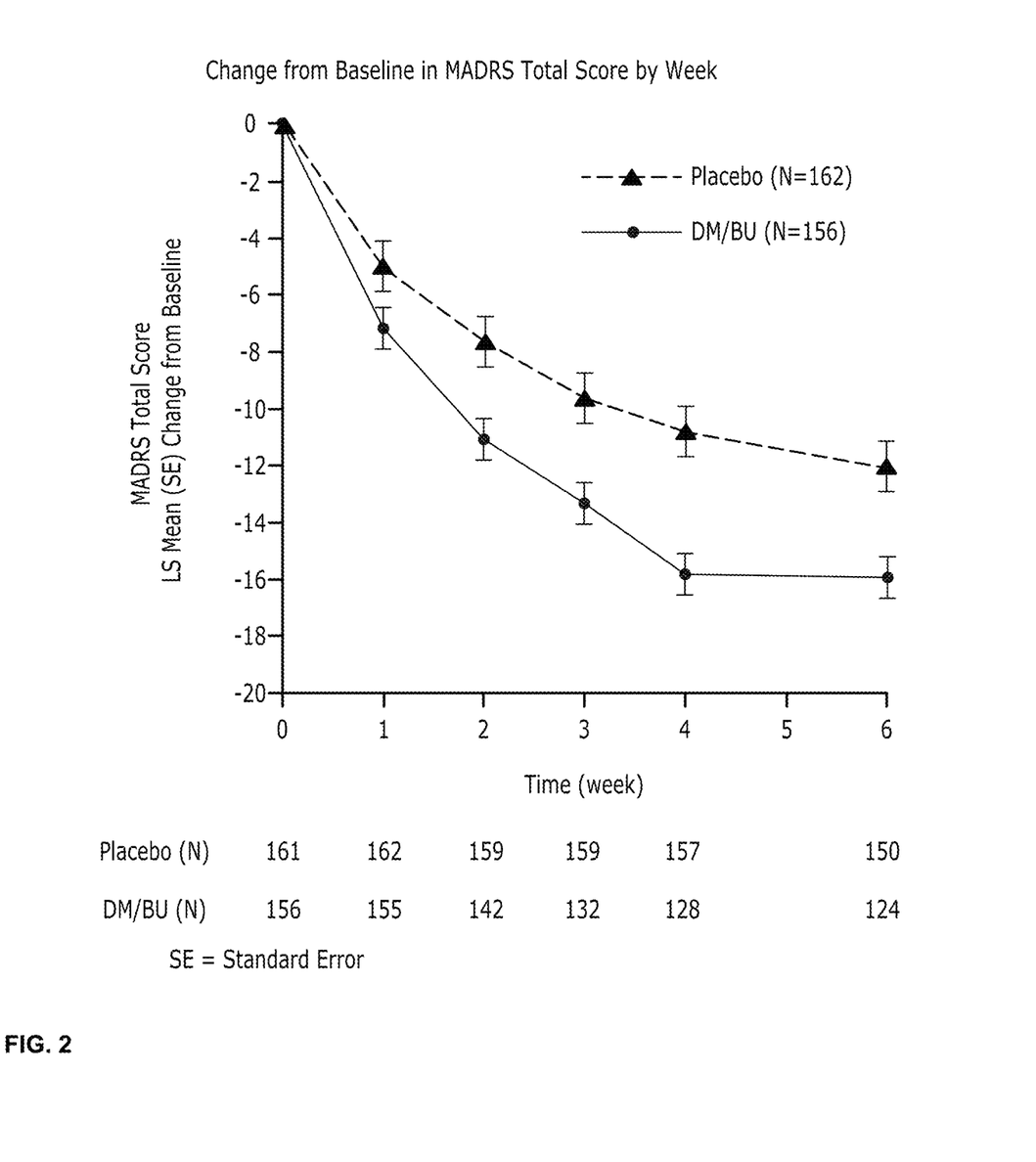
FIG. 2 depicts the change from baseline in MADRS total score by week for human patients receiving a tablet containing 45 mg of dextromethorphan hydrobromide and 105 mg of bupropion hydrochloride twice per day.

The effects of renal impairment, hepatic impairment, and CYP2D6 poor metabolizer status on the exposure to the tablets of Example 4 are summarized in FIG. 1.

Results depicted in FIG. 1 are based on plasma concentrations in human patients after 8 days of twice daily dosing of a tablet containing 45 mg of dextromethorphan hydrobromide and 105 mg of bupropion hydrochloride. Data are GMRs and 90% CIs. References used are the matched healthy subjects for renal and hepatic impairment studies, and extensive or ultra-extensive CYP2D6 metabolizers respectively. AUC represents the area under the plasma concentration-time curve from zero to 12 hours; BUP represents bupropion; CI is confidence interval; $C_{max}$ is maximum plasma concentration; DM represents dextromethorphan; GMRs represents geometric mean ratios; PK represents pharmacokinetics.

In FIG. 1, the results for patients with moderate Renal Impairment are identified as "Group 1," the results for patients with Moderate Hepatic Impairment are identified as "Group 2," and the results for patients who are CYP2D6 Poor Metabolizers are identified as "Group 3." The results are summarized in Table 3 below.

TABLE 3

| Patients | Group | PK Parameter | Change Relative to Reference (90% CI) |
|---|---|---|---|
| Moderate Renal Impairment | 1 | DM AUC | 2.21 (1.24, 3.97) |
| Moderate Renal Impairment | 1 | DM $C_{max}$ | 2.10 (1.17, 3.77) |
| Moderate Renal Impairment | 1 | BUP AUC | 1.80 (1.12, 2.92) |
| Moderate Renal Impairment | 1 | BUP $C_{max}$ | 1.87 (1.07, 3.27) |
| Moderate Hepatic Impairment | 2 | DM AUC | 1.17 (0.85, 1.61) |
| Moderate Hepatic Impairment | 2 | DM $C_{max}$ | 1.21 (0.90, 1.62) |
| Moderate Hepatic Impairment | 2 | BUP AUC | 1.36 (0.86, 2.15) |
| Moderate Hepatic Impairment | 2 | BUP $C_{max}$ | 1.44 (0.90, 2.30) |
| CYP2D6 Poor Metabolizer | 3 | DM AUC | 3.40 (2.08, 5.57) |
| CYP2D6 Poor Metabolizer | 3 | DM $C_{max}$ | 3.00 (1.98, 4.54) |
| CYP2D6 Poor Metabolizer | 3 | BUP AUC | 1.04 (0.77, 1.41) |
| CYP2D6 Poor Metabolizer | 3 | BUP $C_{max}$ | 0.97 (0.67, 1.41) |

For example, for patients having moderate hepatic impairment (Group 2), the $AUC_{0-12}$ and $C_{max}$ of dextromethorphan and bupropion were not significantly different from that for healthy patients.

The mean ratio of $AUC_{0-12}$ of dextromethorphan for patients with moderate hepatic impairment as compared to healthy patients was 1.17, with a 90% confidence interval of 0.85-1.61.

The mean ratio of $C_{max}$ of dextromethorphan for patients with moderate hepatic impairment as compared to healthy patients was 1.21, with a 90% confidence interval of 0.90-1.62.

The mean ratio of $AUC_{0-12}$ of bupropion for patients with moderate hepatic impairment as compared to healthy patients was 1.36, with a 90% confidence interval of 0.86-2.15.

The mean ratio of $C_{max}$ of bupropion for patients with moderate hepatic impairment as compared to healthy patients was 1.44, with a 90% confidence interval of 0.90-2.30.

Based upon these results, no dosage adjustment is recommended in patients known to have mild or moderate hepatic impairment.

For patients having moderate renal impairment, a 2.21-fold increase in dextromethorphan $AUC_{0-12}$, a 2.10-fold increase in dextromethorphan $C_{max}$, a 1.80-fold increase in bupropion $AUC_{0-12}$, and a 1.87-fold increase in bupropion $C_{max}$ were observed.

Based upon these results, dosage adjustment is recommended in patients known to have moderate renal impairment because these patients have higher dextromethorphan and bupropion concentrations than patients with healthy renal function. The recommended total daily dose for patients known to have moderate renal impairment is about 45 mg of dextromethorphan hydrobromide and about 105 mg of bupropion hydrochloride (e.g. one tablet containing about 45 mg of dextromethorphan hydrobromide and about 105 mg of bupropion hydrochloride for administration once daily, such as in the morning), or an equivalent dose of another form dextromethorphan and/or bupropion.

Example 5

The effect of concomitantly administered 20 mg of paroxetine on the dextromethorphan exposure to patients taking, twice daily, the tablet of Example 4 containing 45 mg of dextromethorphan hydrobromide and 105 mg of bupropion hydrochloride was determined. Dextromethorphan $AUC_{0-12}$ was increased 2.69-fold and dextromethorphan $C_{max}$ was increased 2.38-fold as compared to patients taking the tablet twice daily without paroxetine.

Example 6

The efficacy of the tablets of Example 4 for the treatment of major depressive disorder in adults was demonstrated in a placebo-controlled clinical study (Study 1). In this study, adult patients (18 to 65 years of age) who met the Diagnostic and Statistical Manual of Mental Disorders (DSM-5) criteria for MDD were randomized to receive the tablets of Example 1 ("DM/BU," 45 mg of dextromethorphan hydrobromide and 105 mg of bupropion hydrochloride) twice daily (N=156) or placebo twice daily (N=162) for 6 weeks. Patients in Study 1 had a median age of 41 years and were 67% female, 55% Caucasian, 35% Black, and 5% Asian. Here, "N" represents number of adult patients.

The primary outcome measure was the change from baseline to Week 6 in the total score of the Montgomery-Åsberg Depression Rating Scale (MADRS). The MADRS is a clinician-rated scale used to assess the severity of depressive symptoms. Patients are rated on 10 items to assess feelings of sadness, inner tension, reduced sleep or appetite, difficulty concentrating, lassitude, lack of interest, pessimism, and suicidality. Scores on the MADRS range from 0 to 60, with higher scores indicating more severe depression. DM/BU was statistically significantly superior to placebo in improvement of depressive symptoms as measured by decrease in MADRS total score at Week 6 (see Table 4).

TABLE 4

Primary Efficacy Results for Change from Baseline in MADRS Total Score at Week 6 in Adult Patients with MDD

| Study | Treatment Group | Mean Baseline Score (SD) | LS Mean Change from Baseline (SE) | LS Mean Difference[a] (95% CI) |
| --- | --- | --- | --- | --- |
| Study 1 | DM/BU (N = 156) | 33.6 (4.4) | −15.9 (0.9) | −3.9 (−6.4, −1.4) |
|  | Placebo (N = 162) | 33.2 (4.4) | −12.1 (0.9) | — |

SD = standard deviation;
SE = standard error;
LS Mean = least-squares mean;
CI = confidence interval.
[a]drug-placebo The change from baseline in MADRS total score by week is displayed in FIG. 1. The change in MADRS total score from baseline to Week 1 and from baseline to Week 2 were pre-specified secondary efficacy endpoints. The difference between DM/BU and placebo in change from baseline in MADRS total score was statistically significant at Week 1 and at Week 2.

Examination of demographic subgroups by age, sex, and race did not suggest differences in response.

The following documents are incorporated by reference herein in their entireties: PCT/US2023/069655, filed Jul. 5, 2023, U.S. Provisional App. Nos. 63/359,143, filed Jul. 7, 2022; 63/370,592, filed Aug. 5, 2022; 63/396,182, filed Aug. 8, 2022; 63/373,040, filed Aug. 19, 2022; and 63/401,541, filed Aug. 26, 2022; all of which are incorporated by reference herein in their entireties.

Unless otherwise indicated, all numbers expressing quantities of ingredients, properties such as amounts, percentage, and so forth used in the specification and claims are to be understood in all instances as indicating both the exact values as shown and as being modified by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Use of the term "comprising" or "comprises" herein also contemplates that use of "consisting essentially of," "consists essentially of," "consisting of," or "consists of" in its place.

Affirmative recitation of an element anywhere herein should be understood to contemplate both including and excluding that element.

The terms "a," "an," "the" and similar referents used in the context of describing the embodiments (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the embodiments and does not pose a limitation on the scope of any claim. No language in the specification should be construed as indicating any non-claimed element essential to the practice of the claims.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from a group, for reasons of convenience and/or to expedite prosecution. When any such inclusion or deletion occurs, the specification is deemed to contain the group as modified thus fulfilling the written description of all Markush groups if used in the appended claims.

Certain embodiments are described herein, including the best mode known to the inventors for carrying out the claimed embodiments. Of course, variations on these described embodiments will become apparent to those of ordinary skill in the art upon reading the foregoing description. The inventor expects skilled artisans to employ such variations as appropriate, and the inventors intend for the claimed embodiments to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

The invention claimed is:

1. A method of treating major depressive disorder, comprising screening a human patient who is experiencing major depressive disorder to determine if the human patient is receiving any other medications that contain bupropion; and if the human patient is receiving a medication containing bupropion, and concomitant use of the other medication containing bupropion and a tablet containing 45 mg of dextromethorphan hydrobromide and 105 mg of bupropion hydrochloride is clinically warranted, then:

administering the tablet to the human patient once daily in the morning for 3 days, and after 3 days, administering the tablet to the human patient twice daily at least 8 hours apart, and instructing the patient to not crush, divide or chew the tablet, and continuing the concomitant use of the other medication containing bupropion;

monitoring the human patient for a neuropsychiatric reaction, and instructing the human patient to contact a healthcare provider if a neuropsychiatric reaction occurs; and informing the patient of a dose-related risk of seizure associated with bupropion-containing products and immediately discontinuing administration of the tablet if the human patient experiences a seizure.

2. The method of claim 1, further comprising assessing the blood pressure of the human patient and monitoring the blood pressure periodically during treatment.

3. The method of claim 1, further comprising screening the human patient for a personal or family history of bipolar disorder, mania, or hypomania.

4. The method of claim 1, wherein the tablet contains an immediate-release formulation of dextromethorphan hydrobromide.

5. The method of claim 4, wherein the tablet contains an extended-release formulation of bupropion hydrochloride.

6. A method of treating major depressive disorder, comprising screening a human patient who is experiencing major depressive disorder to determine if the human patient is receiving any other medications that contain dextromethorphan; and if the human patient is receiving a medication containing dextromethorphan, and concomitant use of the other medication containing dextromethorphan and a tablet containing 45 mg of dextromethorphan hydrobromide and 105 mg of bupropion hydrochloride is clinically warranted, then:

administering the tablet to the human patient once daily in the morning for 3 days, and after 3 days, administering the tablet to the human patient twice daily at least 8 hours apart, instructing the patient to not crush, divide or chew the tablet, and continuing the concomitant use of the other medication containing dextromethorphan;

informing the human patient of the increased risk for serotonin syndrome, and if the human patient experiences a symptom of serotonin syndrome, immediately discontinuing administration of the tablet, the medication containing dextromethorphan, or both, and initiating supportive symptomatic treatment for the symptom of serotonin syndrome; and monitoring the human patient for a neuropsychiatric reaction, and instructing the human patient to contact a healthcare provider if a neuropsychiatric reaction occurs.

7. The method of claim 6, further comprising assessing the blood pressure of the human patient and monitoring the blood pressure periodically during treatment.

8. The method of claim 6, further comprising screening the human patient for a personal or family history of bipolar disorder, mania, or hypomania.

9. The method of claim 6, wherein the tablet contains an immediate-release formulation of dextromethorphan hydrobromide.

10. The method of claim 9, wherein the tablet contains an extended-release formulation of bupropion hydrochloride.

11. A method of treating major depressive disorder, comprising screening a human patient who is experiencing major depressive disorder to determine if the human patient is receiving a serotonergic drug; and if the patient is a receiving a serotonergic drug and concomitant use of the serotonergic drug, and a tablet containing 45 mg of dextromethorphan hydrobromide and 105 mg of bupropion hydrochloride is clinically warranted, then:

administering the tablet to the human patient once daily in the morning for 3 days, and after 3 days, administering the tablet to the human patient twice daily at least 8 hours apart, instructing the patient to not crush, divide or chew the tablet, and continuing the concomitant use of the serotonergic drug; and informing the human patient of the increased risk for serotonin syndrome, and, if the human patient experiences a symptom of serotonin syndrome, immediately discontinuing administration of the tablet, the serotonergic drug, or both, and initiating supportive symptomatic treatment for the symptom of serotonin syndrome.

12. The method of claim 11, further comprising assessing the blood pressure of the human patient and monitoring the blood pressure periodically during treatment.

13. The method of claim 11, further comprising screening the human patient for a personal or family history of bipolar disorder, mania, or hypomania.

14. The method of claim 11, wherein the tablet contains an immediate-release formulation of dextromethorphan hydrobromide.

15. The method of claim 14, wherein the tablet contains an extended-release formulation of bupropion hydrochloride.

16. The method of claim 11, further comprising monitoring the human patient for a neuropsychiatric reaction, and instructing the human patient to contact a healthcare provider if a neuropsychiatric reaction occurs.

* * * * *

UNITED STATES PATENT AND TRADEMARK OFFICE
CERTIFICATE OF CORRECTION

| | | |
|---|---|---|
| PATENT NO. | : 12,146,889 B1 | Page 1 of 1 |
| APPLICATION NO. | : 18/494550 | |
| DATED | : November 19, 2024 | |
| INVENTOR(S) | : Herriot Tabuteau | |

It is certified that error appears in the above-identified patent and that said Letters Patent is hereby corrected as shown below:

In the Specification

Column 22, Line 63: replace "Example 5" with --Example 6--
Column 23, Line 7: replace "Example 6" with --Example 7--
Column 23, Line 14: replace "Example 1" with --Example 4--
Column 23, Line 52: replace "FIG. 1" with --FIG. 2--

Signed and Sealed this
Eleventh Day of March, 2025

Coke Morgan Stewart
*Acting Director of the United States Patent and Trademark Office*